(12) United States Patent
Boudreaux et al.

(10) Patent No.: US 8,893,946 B2
(45) Date of Patent: Nov. 25, 2014

(54) LAPAROSCOPIC TISSUE THICKNESS AND CLAMP LOAD MEASURING DEVICES

(75) Inventors: Chad P. Boudreaux, Cincinnati, OH (US); Eugene L. Timperman, Cincinnati, OH (US); Leslie M. Fugikawa, Cincinnati, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 1707 days.

(21) Appl. No.: 11/729,008

(22) Filed: Mar. 28, 2007

(65) Prior Publication Data

US 2009/0012556 A1 Jan. 8, 2009

(51) Int. Cl.
| | | |
|---|---|---|
| A61B 17/10 | (2006.01) | |
| A61B 5/107 | (2006.01) | |
| A61B 17/072 | (2006.01) | |
| A61B 17/068 | (2006.01) | |
| A61B 17/29 | (2006.01) | |
| A61B 19/00 | (2006.01) | |

(52) U.S. Cl.
CPC ......... *A61B 17/07207* (2013.01); *A61B 17/068* (2013.01); *A61B 17/072* (2013.01); *A61B 17/29* (2013.01); *A61B 19/46* (2013.01); *A61B 2017/07214* (2013.01); *A61B 2019/461* (2013.01); *A61B 2019/464* (2013.01)
USPC ........ 227/175.1; 600/587; 606/139; 606/205; 606/219; 33/783

(58) Field of Classification Search
USPC ......... 600/300, 546, 547, 550, 561, 562, 563, 600/564, 565, 566, 567, 568, 593, 595; 606/1, 32, 34, 39, 41, 46, 48, 51, 139, 606/142, 213, 215, 219, 220, 221; 227/175.1, 175.2, 175.3, 175.4, 176.1, 227/177.1, 178.1, 179.1, 180.1, 181.1, 227/182.1; 33/783, 784, 787, 788, 792, 33/807; 901/33, 34
See application file for complete search history.

(56) References Cited

U.S. PATENT DOCUMENTS

| 2,804,848 A | 9/1957 | O'Farrell et al. |
| 2,853,074 A | 9/1958 | Olson |

(Continued)

FOREIGN PATENT DOCUMENTS

| CA | 2458946 A1 | 3/2003 |
| CA | 2512960 A1 | 1/2006 |

(Continued)

OTHER PUBLICATIONS

European Search Opinion, Application No. 08251188.2, dated May 7, 2009 (6 pages).

(Continued)

*Primary Examiner* — Max Hindenburg
*Assistant Examiner* — John Pani

(57) ABSTRACT

A surgical instrument having opposed jaws that can be selectively moved between open and closed positions. Various embodiments include components for measuring the thickness of tissue clamped between the opposed jaws. Some embodiments are configured to ascertain the amount of compressive force that is being applied to the tissue while the thickness of the tissue is being determined. The tissue thickness data is displayed on the instrument itself and/or on a display that is remote from the instrument. The various embodiments may comprise different types of surgical instruments such as surgical staplers and graspers. A jaw arrangement with jaws shaped to define a cradle that corresponds to a cross-sectional shape of an object is also disclosed. The components that generate the thickness data may be electrically or mechanically actuated.

17 Claims, 23 Drawing Sheets

(56) References Cited

U.S. PATENT DOCUMENTS

| | | |
|---|---|---|
| 3,490,675 A | 1/1970 | Green et al. |
| 3,551,987 A | 1/1971 | Wilkinson |
| 3,643,851 A | 2/1972 | Green et al. |
| 3,662,939 A | 5/1972 | Bryan |
| 3,717,294 A | 2/1973 | Green |
| 3,819,100 A | 6/1974 | Noiles et al. |
| 4,331,277 A | 5/1982 | Green |
| 4,383,634 A | 5/1983 | Green |
| 4,396,139 A | 8/1983 | Hall et al. |
| 4,402,445 A | 9/1983 | Green |
| 4,415,112 A | 11/1983 | Green |
| 4,429,695 A | 2/1984 | Green |
| 4,475,679 A | 10/1984 | Fleury, Jr. |
| 4,489,875 A | 12/1984 | Crawford et al. |
| 4,500,024 A | 2/1985 | DiGiovanni et al. |
| 4,505,273 A | 3/1985 | Braun et al. |
| 4,505,414 A | 3/1985 | Filipi |
| 4,506,671 A | 3/1985 | Green |
| 4,522,327 A | 6/1985 | Korthoff et al. |
| 4,530,453 A | 7/1985 | Green |
| 4,566,620 A | 1/1986 | Green et al. |
| 4,573,622 A | 3/1986 | Green et al. |
| 4,576,167 A | 3/1986 | Noiles |
| 4,580,712 A | 4/1986 | Green |
| 4,610,250 A | 9/1986 | Green |
| 4,610,383 A | 9/1986 | Rothfuss et al. |
| 4,619,262 A | 10/1986 | Taylor |
| 4,629,107 A | 12/1986 | Fedotov et al. |
| 4,655,222 A | 4/1987 | Florez et al. |
| 4,664,305 A | 5/1987 | Blake, III et al. |
| 4,667,674 A | 5/1987 | Korthoff et al. |
| 4,671,445 A | 6/1987 | Barker et al. |
| 4,715,520 A | 12/1987 | Roehr, Jr. et al. |
| 4,728,020 A | 3/1988 | Green et al. |
| 4,752,024 A | 6/1988 | Green et al. |
| 4,754,909 A | 7/1988 | Barker et al. |
| 4,767,044 A | 8/1988 | Green |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,869,414 A | 9/1989 | Green et al. |
| 4,869,415 A | 9/1989 | Fox |
| 4,880,015 A | 11/1989 | Nierman |
| 4,941,623 A | 7/1990 | Pruitt |
| 4,944,443 A | 7/1990 | Oddsen et al. |
| 5,014,899 A | 5/1991 | Presty et al. |
| 5,042,707 A | 8/1991 | Taheri |
| 5,065,929 A | 11/1991 | Schulze et al. |
| 5,071,430 A | 12/1991 | de Salis et al. |
| 5,084,057 A | 1/1992 | Green et al. |
| 5,116,349 A | 5/1992 | Aranyi |
| 5,129,570 A | 7/1992 | Schulze et al. |
| 5,137,198 A | 8/1992 | Nobis et al. |
| 5,139,513 A | 8/1992 | Segato |
| 5,158,567 A | 10/1992 | Green |
| 5,171,247 A | 12/1992 | Hughett et al. |
| 5,171,249 A | 12/1992 | Stefanchik et al. |
| 5,209,747 A | 5/1993 | Knoepfler |
| 5,211,649 A | 5/1993 | Kohler et al. |
| 5,221,036 A | 6/1993 | Takase |
| 5,222,975 A | 6/1993 | Crainich |
| 5,236,440 A | 8/1993 | Hlavacek |
| 5,246,443 A | 9/1993 | Mai |
| 5,258,009 A | 11/1993 | Conners |
| 5,282,806 A | 2/1994 | Haber et al. |
| 5,282,829 A | 2/1994 | Hermes |
| 5,304,204 A | 4/1994 | Bregen |
| 5,314,424 A | 5/1994 | Nicholas |
| 5,333,422 A | 8/1994 | Warren et al. |
| 5,341,724 A | 8/1994 | Vatel |
| 5,342,395 A | 8/1994 | Jarrett et al. |
| 5,342,396 A | 8/1994 | Cook |
| 5,350,400 A | 9/1994 | Esposito et al. |
| 5,352,235 A | 10/1994 | Koros et al. |
| 5,352,238 A | 10/1994 | Green et al. |
| 5,354,303 A | 10/1994 | Spaeth et al. |
| 5,358,510 A | 10/1994 | Luscombe et al. |
| 5,366,479 A | 11/1994 | McGarry et al. |
| 5,374,277 A | 12/1994 | Hassler |
| 5,379,933 A | 1/1995 | Green et al. |
| 5,383,880 A | 1/1995 | Hooven |
| 5,383,888 A | 1/1995 | Zvenyatsky et al. |
| 5,383,895 A | 1/1995 | Holmes et al. |
| 5,389,098 A | 2/1995 | Tsuruta et al. |
| 5,397,324 A | 3/1995 | Carroll et al. |
| 5,405,344 A | 4/1995 | Williamson et al. |
| 5,413,272 A | 5/1995 | Green et al. |
| 5,415,334 A | 5/1995 | Williamson, IV et al. |
| 5,417,361 A | 5/1995 | Williamson, IV |
| 5,425,745 A | 6/1995 | Green et al. |
| 5,449,365 A | 9/1995 | Green et al. |
| 5,456,401 A | 10/1995 | Green et al. |
| 5,474,566 A | 12/1995 | Alesi et al. |
| 5,478,354 A | 12/1995 | Tovey et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,497,933 A | 3/1996 | DeFonzo et al. |
| 5,503,320 A | 4/1996 | Webster et al. |
| 5,503,638 A | 4/1996 | Cooper et al. |
| 5,509,596 A | 4/1996 | Green et al. |
| 5,529,235 A | 6/1996 | Boiarski et al. |
| 5,533,521 A | 7/1996 | Granger |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,547,117 A | 8/1996 | Hamblin et al. |
| 5,549,628 A | 8/1996 | Cooper et al. |
| 5,549,637 A | 8/1996 | Crainich |
| 5,553,765 A | 9/1996 | Knodel et al. |
| 5,554,169 A | 9/1996 | Green et al. |
| 5,558,665 A | 9/1996 | Kieturakis |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,702 A | 10/1996 | Huitema et al. |
| 5,564,615 A | 10/1996 | Bishop et al. |
| 5,571,116 A | 11/1996 | Bolanos et al. |
| 5,575,799 A | 11/1996 | Bolanos et al. |
| 5,575,803 A | 11/1996 | Cooper et al. |
| 5,577,654 A | 11/1996 | Bishop |
| 5,579,978 A | 12/1996 | Green et al. |
| 5,580,067 A | 12/1996 | Hamblin et al. |
| 5,582,611 A | 12/1996 | Tsuruta et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,609,285 A | 3/1997 | Grant et al. |
| 5,624,452 A | 4/1997 | Yates |
| 5,628,446 A | 5/1997 | Geiste et al. |
| 5,630,539 A | 5/1997 | Plyley et al. |
| 5,630,540 A | 5/1997 | Blewett |
| 5,632,432 A | 5/1997 | Schulze et al. |

(56) References Cited

U.S. PATENT DOCUMENTS

| | | | |
|---|---|---|---|
| 5,632,433 | A | 5/1997 | Grant et al. |
| 5,634,584 | A | 6/1997 | Okorocha et al. |
| 5,636,779 | A | 6/1997 | Palmer |
| 5,636,780 | A | 6/1997 | Green et al. |
| 5,639,008 | A | 6/1997 | Gallagher et al. |
| 5,645,209 | A | 7/1997 | Green et al. |
| 5,647,526 | A | 7/1997 | Green et al. |
| 5,649,937 | A | 7/1997 | Bito et al. |
| 5,651,491 | A | 7/1997 | Heaton et al. |
| 5,653,373 | A | 8/1997 | Green et al. |
| 5,653,374 | A | 8/1997 | Young et al. |
| 5,655,698 | A | 8/1997 | Yoon |
| 5,657,921 | A | 8/1997 | Young et al. |
| 5,662,258 | A | 9/1997 | Knodel et al. |
| 5,662,260 | A | 9/1997 | Yoon |
| 5,667,527 | A | 9/1997 | Cook |
| 5,669,544 | A | 9/1997 | Schulze et al. |
| 5,673,840 | A | 10/1997 | Schulze et al. |
| 5,673,841 | A | 10/1997 | Schulze et al. |
| 5,673,842 | A | 10/1997 | Bittner et al. |
| 5,678,748 | A | 10/1997 | Plyley et al. |
| 5,680,981 | A | 10/1997 | Mililli et al. |
| 5,680,982 | A | 10/1997 | Schulze et al. |
| 5,680,983 | A | 10/1997 | Plyley et al. |
| 5,685,474 | A | 11/1997 | Seeber |
| 5,688,270 | A | 11/1997 | Yates et al. |
| 5,690,269 | A | 11/1997 | Bolanos et al. |
| 5,692,668 | A | 12/1997 | Schulze et al. |
| 5,697,543 | A | 12/1997 | Burdorff |
| 5,700,270 | A | 12/1997 | Peyser et al. |
| 5,702,408 | A | 12/1997 | Wales et al. |
| 5,704,534 | A | 1/1998 | Huitema et al. |
| 5,706,997 | A | 1/1998 | Green et al. |
| 5,706,998 | A | 1/1998 | Plyley et al. |
| 5,707,392 | A | 1/1998 | Kortenbach |
| 5,709,334 | A | 1/1998 | Sorrentino et al. |
| 5,711,472 | A | 1/1998 | Bryan |
| 5,713,505 | A | 2/1998 | Huitema |
| 5,715,987 | A | 2/1998 | Kelley et al. |
| 5,715,988 | A | 2/1998 | Palmer |
| 5,716,366 | A | 2/1998 | Yates |
| 5,718,359 | A | 2/1998 | Palmer et al. |
| 5,718,360 | A | 2/1998 | Green et al. |
| 5,725,536 | A | 3/1998 | Oberlin et al. |
| 5,725,554 | A | 3/1998 | Simon et al. |
| 5,728,121 | A | 3/1998 | Bimbo et al. |
| 5,730,758 | A | 3/1998 | Allgeyer |
| 5,732,871 | A | 3/1998 | Clark et al. |
| 5,732,872 | A | 3/1998 | Bolduc et al. |
| 5,735,445 | A | 4/1998 | Vidal et al. |
| 5,735,874 | A | 4/1998 | Measamer et al. |
| 5,743,456 | A | 4/1998 | Jones et al. |
| 5,752,644 | A | 5/1998 | Bolanos et al. |
| 5,758,814 | A | 6/1998 | Gallagher et al. |
| 5,762,255 | A | 6/1998 | Chrisman et al. |
| 5,762,256 | A | 6/1998 | Mastri et al. |
| 5,779,130 | A | 7/1998 | Alesi et al. |
| 5,779,131 | A | 7/1998 | Knodel et al. |
| 5,779,132 | A | 7/1998 | Knodel et al. |
| 5,782,396 | A | 7/1998 | Mastri et al. |
| 5,782,397 | A | 7/1998 | Koukline |
| 5,785,232 | A | 7/1998 | Vidal et al. |
| 5,794,834 | A | 8/1998 | Hamblin et al. |
| 5,797,536 | A | 8/1998 | Smith et al. |
| 5,797,537 | A | 8/1998 | Oberlin et al. |
| 5,797,538 | A | 8/1998 | Heaton et al. |
| 5,797,959 | A | 8/1998 | Castro et al. |
| 5,799,857 | A | 9/1998 | Robertson et al. |
| 5,807,393 | A | 9/1998 | Williamson, IV et al. |
| 5,817,119 | A | 10/1998 | Klieman et al. |
| 5,820,009 | A | 10/1998 | Melling et al. |
| 5,826,776 | A | 10/1998 | Schulze et al. |
| 5,829,662 | A | 11/1998 | Allen et al. |
| 5,833,690 | A | 11/1998 | Yates et al. |
| 5,833,695 | A | 11/1998 | Yoon |
| 5,836,503 | A | 11/1998 | Ehrenfels et al. |
| 5,839,639 | A | 11/1998 | Sauer et al. |
| 5,855,311 | A | 1/1999 | Hamblin et al. |
| 5,865,361 | A | 2/1999 | Milliman et al. |
| 5,868,760 | A | 2/1999 | McGuckin, Jr. |
| 5,871,135 | A | 2/1999 | Williamson, IV et al. |
| 5,876,401 | A | 3/1999 | Schulze et al. |
| 5,878,937 | A | 3/1999 | Green et al. |
| 5,878,938 | A | 3/1999 | Bittner et al. |
| 5,893,506 | A | 4/1999 | Powell |
| 5,894,979 | A | 4/1999 | Powell |
| 5,897,552 | A | 4/1999 | Edwards et al. |
| 5,901,895 | A | 5/1999 | Heaton et al. |
| 5,906,625 | A | 5/1999 | Bito et al. |
| 5,908,427 | A | 6/1999 | McKean et al. |
| 5,911,353 | A | 6/1999 | Bolanos et al. |
| 5,915,616 | A | 6/1999 | Viola et al. |
| 5,918,791 | A | 7/1999 | Sorrentino et al. |
| 5,919,198 | A | 7/1999 | Graves, Jr. et al. |
| 5,938,667 | A | 8/1999 | Peyser et al. |
| 5,941,442 | A | 8/1999 | Geiste et al. |
| 5,951,552 | A | 9/1999 | Long et al. |
| 5,951,574 | A | 9/1999 | Stefanchik et al. |
| 5,954,259 | A | 9/1999 | Viola et al. |
| 5,988,479 | A | 11/1999 | Palmer |
| 6,010,054 | A | 1/2000 | Johnson et al. |
| 6,032,849 | A | 3/2000 | Mastri et al. |
| 6,033,427 | A | 3/2000 | Lee |
| 6,045,560 | A | 4/2000 | McKean et al. |
| 6,050,472 | A | 4/2000 | Shibata |
| 6,083,242 | A | 7/2000 | Cook |
| 6,086,600 | A | 7/2000 | Kortenbach |
| 6,099,551 | A | 8/2000 | Gabbay |
| 6,102,271 | A | 8/2000 | Longo et al. |
| 6,109,500 | A | 8/2000 | Alli et al. |
| 6,117,158 | A | 9/2000 | Measamer et al. |
| 6,119,913 | A | 9/2000 | Adams et al. |
| 6,126,058 | A | 10/2000 | Adams et al. |
| 6,131,789 | A | 10/2000 | Schulze et al. |
| 6,155,473 | A | 12/2000 | Tompkins et al. |
| 6,156,056 | A | 12/2000 | Kearns et al. |
| 6,162,208 | A | 12/2000 | Hipps |
| 6,168,605 | B1 | 1/2001 | Measamer et al. |
| 6,171,330 | B1 | 1/2001 | Benchetrit |
| 6,197,042 | B1 | 3/2001 | Ginn et al. |
| 6,202,914 | B1 | 3/2001 | Geiste et al. |
| 6,228,084 | B1 | 5/2001 | Kirwan, Jr. |
| 6,241,139 | B1 | 6/2001 | Milliman et al. |
| 6,241,723 | B1 | 6/2001 | Heim et al. |
| 6,250,532 | B1 | 6/2001 | Green et al. |
| 6,264,086 | B1 | 7/2001 | McGuckin, Jr. |
| 6,264,087 | B1 | 7/2001 | Whitman |
| 6,273,897 | B1 | 8/2001 | Dalessandro et al. |
| 6,302,311 | B1 | 10/2001 | Adams et al. |
| 6,315,184 | B1 | 11/2001 | Whitman |
| 6,325,810 | B1 | 12/2001 | Hamilton et al. |
| 6,330,965 | B1 | 12/2001 | Milliman et al. |
| 6,387,113 | B1 | 5/2002 | Hawkins et al. |
| 6,387,114 | B2 | 5/2002 | Adams |
| 6,406,440 | B1 | 6/2002 | Stefanchik |
| RE37,814 | E | 8/2002 | Allgeyer |
| 6,436,107 | B1 | 8/2002 | Wang et al. |
| 6,443,973 | B1 | 9/2002 | Whitman |
| 6,482,200 | B2 | 11/2002 | Shippert |
| 6,488,197 | B1 | 12/2002 | Whitman |
| 6,491,201 | B1 | 12/2002 | Whitman |
| 6,494,896 | B1 | 12/2002 | D'Alessio et al. |
| 6,503,257 | B2 | 1/2003 | Grant et al. |
| 6,505,768 | B2 | 1/2003 | Whitman |
| 6,517,565 | B1 | 2/2003 | Whitman et al. |
| 6,569,171 | B2 | 5/2003 | DeGuillebon et al. |
| 6,578,751 | B2 | 6/2003 | Hartwick |
| 6,588,643 | B2 | 7/2003 | Bolduc et al. |
| 6,592,597 | B2 | 7/2003 | Grant et al. |
| 6,601,749 | B2 | 8/2003 | Sullivan et al. |
| 6,602,252 | B2 | 8/2003 | Mollenauer |
| 6,616,686 | B2 | 9/2003 | Coleman et al. |
| 6,619,529 | B2 | 9/2003 | Green et al. |
| 6,620,166 | B1 | 9/2003 | Wenstrom, Jr. et al. |

(56) References Cited

U.S. PATENT DOCUMENTS

| | | | |
|---|---|---|---|
| 6,629,988 B2 | 10/2003 | Weadock |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,681,979 B2 | 1/2004 | Whitman |
| 6,682,528 B2 | 1/2004 | Frazier et al. |
| 6,685,727 B2 | 2/2004 | Fisher et al. |
| 6,695,199 B2 | 2/2004 | Whitman |
| 6,698,643 B2 | 3/2004 | Whitman |
| 6,716,233 B1 | 4/2004 | Whitman |
| 6,723,087 B2 | 4/2004 | O'Neill et al. |
| 6,752,768 B2 | 6/2004 | Burdorff et al. |
| 6,755,338 B2 | 6/2004 | Hahnen et al. |
| 6,767,356 B2 | 7/2004 | Kanner et al. |
| 6,769,594 B2 | 8/2004 | Orban, III |
| 6,773,438 B1 | 8/2004 | Knodel et al. |
| 6,786,382 B1 | 9/2004 | Hoffman |
| 6,786,896 B1 | 9/2004 | Madhani et al. |
| 6,793,652 B1 | 9/2004 | Whitman et al. |
| 6,805,273 B2 | 10/2004 | Bilotti et al. |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,821,273 B2 | 11/2004 | Mollenauer |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| RE38,708 E | 3/2005 | Bolanos et al. |
| 6,874,669 B2 | 4/2005 | Adams et al. |
| 6,877,647 B2 | 4/2005 | Green et al. |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 7,000,818 B2 | 2/2006 | Shelton, IV et al. |
| 7,000,819 B2 | 2/2006 | Swayze et al. |
| 7,001,408 B2 | 2/2006 | Knodel et al. |
| 7,008,435 B2 | 3/2006 | Cummins |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,048,687 B1 | 5/2006 | Reuss et al. |
| 7,055,730 B2 | 6/2006 | Ehrenfels et al. |
| 7,055,731 B2 | 6/2006 | Shelton, IV et al. |
| 7,056,330 B2 | 6/2006 | Gayton |
| 7,059,508 B2 | 6/2006 | Shelton, IV et al. |
| 7,070,083 B2 | 7/2006 | Jankowski |
| 7,077,856 B2 | 7/2006 | Whitman |
| 7,080,769 B2 | 7/2006 | Vresh et al. |
| 7,081,114 B2 | 7/2006 | Rashidi |
| 7,083,073 B2 | 8/2006 | Yoshie et al. |
| 7,083,075 B2 | 8/2006 | Swayze et al. |
| 7,090,673 B2 | 8/2006 | Dycus et al. |
| 7,090,684 B2 | 8/2006 | McGuckin, Jr. et al. |
| 7,097,089 B2 | 8/2006 | Marczyk |
| 7,108,695 B2 | 9/2006 | Witt et al. |
| 7,108,709 B2 | 9/2006 | Cummins |
| 7,111,769 B2 | 9/2006 | Wales et al. |
| 7,112,214 B2 | 9/2006 | Peterson et al. |
| 7,114,642 B2 | 10/2006 | Whitman |
| 7,118,582 B1 | 10/2006 | Wang et al. |
| 7,121,446 B2 | 10/2006 | Arad et al. |
| 7,122,028 B2 | 10/2006 | Looper et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,160,299 B2 | 1/2007 | Baily |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,207,472 B2 | 4/2007 | Wukusick et al. |
| 7,210,609 B2 | 5/2007 | Leiboff et |
| 7,213,736 B2 | 5/2007 | Wales et al. |
| 7,220,272 B2 | 5/2007 | Weadock |
| 7,225,964 B2 | 6/2007 | Mastri et al. |
| 7,235,089 B1 | 6/2007 | McGuckin, Jr. |
| 7,238,195 B2 | 7/2007 | Viola |
| 7,241,288 B2 | 7/2007 | Braun |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,296,724 B2 | 11/2007 | Green et al. |
| 7,297,149 B2 | 11/2007 | Vitali et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,556 B2 | 12/2007 | Metzger |
| 7,328,828 B2 | 2/2008 | Ortiz et al. |
| 7,328,829 B2 | 2/2008 | Arad et al. |
| 7,343,920 B2 | 3/2008 | Toby et al. |
| 7,354,447 B2 | 4/2008 | Shelton, IV et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,398,908 B2 | 7/2008 | Holsten et al. |
| 7,404,508 B2 | 7/2008 | Smith et al. |
| 7,404,509 B2 | 7/2008 | Ortiz et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,473,253 B2 | 1/2009 | Dycus et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,546,940 B2 | 6/2009 | Milliman et al. |
| 7,549,564 B2 | 6/2009 | Boudreaux |
| 7,552,854 B2 | 6/2009 | Wixey et al. |

(56) References Cited

U.S. PATENT DOCUMENTS

| | | |
|---|---|---|
| 7,568,603 B2 | 8/2009 | Shelton, IV et al. |
| 7,575,144 B2 | 8/2009 | Ortiz et al. |
| 7,631,793 B2 | 12/2009 | Rethy et al. |
| 7,641,093 B2 | 1/2010 | Doll et al. |
| 7,665,646 B2 | 2/2010 | Prommersberger |
| 7,699,204 B2 | 4/2010 | Viola |
| 8,079,606 B2 | 12/2011 | Dull et al. |
| 2002/0117534 A1 | 8/2002 | Green et al. |
| 2002/0165541 A1 | 11/2002 | Whitman |
| 2004/0006372 A1 | 1/2004 | Racenet et al. |
| 2004/0034369 A1 | 2/2004 | Sauer et al. |
| 2004/0044364 A1 | 3/2004 | DeVries et al. |
| 2004/0094597 A1 | 5/2004 | Whitman et al. |
| 2004/0108357 A1 | 6/2004 | Milliman et al. |
| 2004/0111081 A1 | 6/2004 | Whitman et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0222268 A1 | 11/2004 | Bilotti et al. |
| 2004/0232201 A1 | 11/2004 | Wenchell et al. |
| 2004/0243151 A1 | 12/2004 | Demmy et al. |
| 2004/0243176 A1 | 12/2004 | Hahnen et al. |
| 2004/0254608 A1 | 12/2004 | Huitema et al. |
| 2005/0033357 A1 | 2/2005 | Braun |
| 2005/0054946 A1 | 3/2005 | Krzyzanowski |
| 2005/0059997 A1 | 3/2005 | Bauman et al. |
| 2005/0080454 A1 | 4/2005 | Drews et al. |
| 2005/0103819 A1 | 5/2005 | Racenet et al. |
| 2005/0107824 A1 | 5/2005 | Hillstead et al. |
| 2005/0119669 A1 | 6/2005 | Demmy |
| 2005/0125009 A1 | 6/2005 | Perry et al. |
| 2005/0131390 A1* | 6/2005 | Heinrich et al. .................. 606/1 |
| 2005/0131457 A1 | 6/2005 | Douglas et al. |
| 2005/0143759 A1 | 6/2005 | Kelly |
| 2005/0171522 A1 | 8/2005 | Christopherson |
| 2005/0184121 A1 | 8/2005 | Heinrich |
| 2005/0187576 A1 | 8/2005 | Whitman et al. |
| 2005/0189397 A1 | 9/2005 | Jankowski |
| 2005/0192628 A1 | 9/2005 | Viola |
| 2005/0216055 A1 | 9/2005 | Scirica et al. |
| 2005/0240222 A1 | 10/2005 | Shipp |
| 2005/0256522 A1* | 11/2005 | Francischelli et al. .......... 606/41 |
| 2005/0263563 A1 | 12/2005 | Racenet et al. |
| 2005/0274768 A1 | 12/2005 | Cummins et al. |
| 2006/0011699 A1 | 1/2006 | Olson et al. |
| 2006/0047303 A1 | 3/2006 | Ortiz et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0085031 A1 | 4/2006 | Bettuchi |
| 2006/0085033 A1 | 4/2006 | Criscuolo et al. |
| 2006/0100643 A1 | 5/2006 | Laufer et al. |
| 2006/0108393 A1 | 5/2006 | Heinrich et al. |
| 2006/0122636 A1 | 6/2006 | Bailly et al. |
| 2006/0149163 A1 | 7/2006 | Hibner et al. |
| 2006/0151567 A1 | 7/2006 | Roy |
| 2006/0180634 A1 | 8/2006 | Shelton, IV et al. |
| 2006/0217729 A1 | 9/2006 | Eskridge et al. |
| 2006/0226196 A1 | 10/2006 | Hueil et al. |
| 2006/0235469 A1 | 10/2006 | Viola |
| 2006/0241655 A1 | 10/2006 | Viola |
| 2006/0241692 A1 | 10/2006 | McGuckin, Jr. et al. |
| 2006/0273135 A1* | 12/2006 | Beetel .......................... 227/175.1 |
| 2006/0278680 A1 | 12/2006 | Viola et al. |
| 2006/0278681 A1 | 12/2006 | Viola et al. |
| 2006/0289602 A1 | 12/2006 | Wales et al. |
| 2007/0023476 A1 | 2/2007 | Whitman et al. |
| 2007/0023477 A1 | 2/2007 | Whitman et al. |
| 2007/0027469 A1 | 2/2007 | Smith et al. |
| 2007/0034668 A1 | 2/2007 | Holsten et al. |
| 2007/0045379 A1 | 3/2007 | Shelton, IV |
| 2007/0055219 A1 | 3/2007 | Whitman et al. |
| 2007/0073341 A1 | 3/2007 | Smith et al. |
| 2007/0084897 A1 | 4/2007 | Shelton, IV et al. |
| 2007/0102452 A1 | 5/2007 | Shelton, IV et al. |
| 2007/0102453 A1 | 5/2007 | Morgan et al. |
| 2007/0102472 A1 | 5/2007 | Shelton, IV |
| 2007/0102473 A1 | 5/2007 | Shelton, IV et al. |
| 2007/0102474 A1 | 5/2007 | Shelton, IV et al. |
| 2007/0106317 A1 | 5/2007 | Shelton, IV et al. |
| 2007/0114261 A1 | 5/2007 | Ortiz et al. |
| 2007/0158385 A1 | 7/2007 | Hueil et al. |
| 2007/0170225 A1 | 7/2007 | Shelton, IV et al. |
| 2007/0173806 A1 | 7/2007 | Orszulak et al. |
| 2007/0173813 A1 | 7/2007 | Odom |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175964 A1 | 8/2007 | Shelton, IV et al. |
| 2007/0179476 A1 | 8/2007 | Shelton, IV et al. |
| 2007/0181632 A1 | 8/2007 | Milliman |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0233053 A1 | 10/2007 | Shelton et al. |
| 2007/0246505 A1 | 10/2007 | Pace-Floridia et al. |
| 2007/0288044 A1 | 12/2007 | Jinno et al. |
| 2007/0295780 A1 | 12/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082124 A1 | 4/2008 | Hess et al. |
| 2008/0082125 A1 | 4/2008 | Murray et al. |
| 2008/0082126 A1 | 4/2008 | Murray et al. |
| 2008/0083813 A1 | 4/2008 | Zemlok et al. |
| 2008/0140115 A1 | 6/2008 | Stopek |
| 2008/0164296 A1 | 7/2008 | Shelton et al. |
| 2008/0167522 A1 | 7/2008 | Giordano et al. |
| 2008/0167644 A1 | 7/2008 | Shelton et al. |
| 2008/0167670 A1 | 7/2008 | Shelton et al. |
| 2008/0167671 A1 | 7/2008 | Giordano et al. |
| 2008/0167672 A1 | 7/2008 | Giordano et al. |
| 2008/0167736 A1 | 7/2008 | Swayze et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0197167 A1 | 8/2008 | Viola et al. |
| 2008/0210738 A1 | 9/2008 | Shelton et al. |
| 2008/0237296 A1 | 10/2008 | Boudreaux et al. |
| 2008/0251568 A1 | 10/2008 | Zemlok et al. |
| 2008/0283570 A1 | 11/2008 | Boyden et al. |
| 2008/0290134 A1 | 11/2008 | Bettuchi et al. |
| 2008/0296343 A1 | 12/2008 | Schall et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |
| 2008/0300579 A1 | 12/2008 | Broehl et al. |
| 2008/0300580 A1 | 12/2008 | Shelton, IV et al. |
| 2008/0300613 A1 | 12/2008 | Shelton, IV et al. |
| 2008/0308601 A1 | 12/2008 | Timm et al. |

(56) References Cited

U.S. PATENT DOCUMENTS

| | | |
|---|---|---|
| 2008/0308602 A1 | 12/2008 | Timm et al. |
| 2008/0308603 A1 | 12/2008 | Shelton et al. |
| 2008/0308606 A1 | 12/2008 | Timm et al. |
| 2008/0308607 A1 | 12/2008 | Timm et al. |
| 2008/0308608 A1 | 12/2008 | Prommersberger |
| 2008/0314954 A1 | 12/2008 | Boudreaux |
| 2008/0314955 A1 | 12/2008 | Boudreaux et al. |
| 2008/0314957 A1 | 12/2008 | Boudreaux |
| 2008/0314960 A1 | 12/2008 | Marczyk et al. |
| 2008/0314961 A1 | 12/2008 | Boudreaux et al. |
| 2008/0314962 A1 | 12/2008 | Boudreaux |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0076534 A1 | 3/2009 | Shelton, IV et al. |
| 2009/0090763 A1 | 4/2009 | Zemlok et al. |
| 2009/0200355 A1 | 8/2009 | Baxter, III et al. |
| 2009/0206123 A1 | 8/2009 | Doll et al. |
| 2009/0206124 A1 | 8/2009 | Hall et al. |
| 2009/0206125 A1 | 8/2009 | Huitema et al. |
| 2009/0206126 A1 | 8/2009 | Huitema et al. |
| 2009/0206128 A1 | 8/2009 | Hueil et al. |
| 2009/0206129 A1 | 8/2009 | Doll et al. |
| 2009/0206130 A1 | 8/2009 | Hall et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206134 A1 | 8/2009 | Swayze et al. |
| 2009/0206135 A1 | 8/2009 | Hall et al. |
| 2009/0206136 A1 | 8/2009 | Moore et al. |
| 2009/0206137 A1 | 8/2009 | Hall et al. |
| 2009/0206138 A1 | 8/2009 | Smith et al. |
| 2009/0206139 A1 | 8/2009 | Hall et al. |
| 2009/0206140 A1 | 8/2009 | Scheib et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0206144 A1 | 8/2009 | Doll et al. |
| 2009/0209946 A1 | 8/2009 | Swayze et al. |
| 2009/0218384 A1 | 9/2009 | Aranyi |
| 2009/0242610 A1 | 10/2009 | Shelton, IV et al. |
| 2009/0255974 A1 | 10/2009 | Viola |
| 2009/0255975 A1 | 10/2009 | Zemlok et al. |
| 2009/0255977 A1 | 10/2009 | Zemlok |
| 2009/0255978 A1 | 10/2009 | Viola et al. |
| 2009/0265976 A1 | 10/2009 | Mclemore |
| 2009/0289096 A1 | 11/2009 | Shelton, IV et al. |
| 2009/0292283 A1 | 11/2009 | Odom |
| 2010/0032470 A1 | 2/2010 | Hess et al. |
| 2010/0065605 A1 | 3/2010 | Shelton, IV et al. |
| 2010/0065609 A1 | 3/2010 | Schwemberger |
| 2010/0069942 A1 | 3/2010 | Shelton, IV |
| 2010/0072251 A1 | 3/2010 | Baxter, III et al. |
| 2010/0072252 A1 | 3/2010 | Baxter, III et al. |
| 2010/0072253 A1 | 3/2010 | Baxter, III et al. |
| 2010/0072256 A1 | 3/2010 | Baxter, III et al. |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089974 A1 | 4/2010 | Shelton, IV |
| 2010/0096435 A1 | 4/2010 | Fuchs et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0179382 A1 | 7/2010 | Shelton, IV et al. |
| 2010/0181364 A1 | 7/2010 | Shelton, IV et al. |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0213241 A1 | 8/2010 | Bedi |
| 2010/0222901 A1 | 9/2010 | Swayze et al. |
| 2010/0224669 A1 | 9/2010 | Shelton, IV et al. |
| 2010/0237132 A1 | 9/2010 | Measamer et al. |
| 2010/0243709 A1 | 9/2010 | Hess et al. |
| 2010/0264193 A1 | 10/2010 | Huang et al. |
| 2010/0264194 A1 | 10/2010 | Huang et al. |
| 2010/0294829 A1 | 11/2010 | Giordano et al. |

FOREIGN PATENT DOCUMENTS

| | | |
|---|---|---|
| CA | 2514274 A1 | 1/2006 |
| DE | 9412228 U | 9/1994 |
| DE | 19924311 A1 | 11/2000 |
| DE | 69328576 T2 | 1/2001 |
| DE | 10314072 A1 | 10/2004 |
| EP | 0122046 A1 | 10/1984 |
| EP | 0070230 B1 | 10/1985 |
| EP | 0033548 B1 | 5/1986 |
| EP | 0276104 A2 | 7/1988 |
| EP | 0639349 A2 | 2/1994 |
| EP | 0324636 B1 | 3/1994 |
| EP | 0593920 A1 | 4/1994 |
| EP | 0600182 A2 | 6/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0653189 A2 | 5/1995 |
| EP | 0669104 A1 | 8/1995 |
| EP | 0511470 B1 | 10/1995 |
| EP | 0679367 A2 | 11/1995 |
| EP | 0392547 B1 | 12/1995 |
| EP | 0685204 A1 | 12/1995 |
| EP | 0699418 A1 | 3/1996 |
| EP | 0702937 A1 | 3/1996 |
| EP | 0705571 A1 | 4/1996 |
| EP | 0484677 B2 | 6/1996 |
| EP | 0541987 B1 | 7/1996 |
| EP | 0667119 B1 | 7/1996 |
| EP | 0770355 A1 | 5/1997 |
| EP | 0503662 B1 | 6/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0676173 B1 | 9/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0760230 B1 | 2/1999 |
| EP | 0537572 B1 | 6/1999 |
| EP | 0552050 B1 | 5/2000 |
| EP | 1090592 A1 | 4/2001 |
| EP | 1256318 B1 | 5/2001 |
| EP | 0908152 B1 | 1/2002 |
| EP | 0872213 B1 | 5/2002 |
| EP | 1238634 A2 | 9/2002 |
| EP | 0656188 B1 | 1/2003 |
| EP | 0829235 B1 | 6/2003 |
| EP | 0813843 B1 | 10/2003 |
| EP | 0741996 B1 | 2/2004 |
| EP | 0705570 B1 | 4/2004 |
| EP | 1086713 B1 | 5/2004 |
| EP | 1426012 A1 | 6/2004 |
| EP | 0888749 B1 | 9/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 1520521 A1 | 4/2005 |
| EP | 1520523 A1 | 4/2005 |
| EP | 1520525 A1 | 4/2005 |

(56) References Cited

FOREIGN PATENT DOCUMENTS

| | | |
|---|---|---|
| EP | 1522264 A1 | 4/2005 |
| EP | 1550408 A1 | 7/2005 |
| EP | 1557129 A1 | 7/2005 |
| EP | 1064883 B1 | 8/2005 |
| EP | 1157666 B1 | 9/2005 |
| EP | 1621138 A2 | 2/2006 |
| EP | 1621139 A2 | 2/2006 |
| EP | 1621141 A2 | 2/2006 |
| EP | 1621145 A2 | 2/2006 |
| EP | 1621151 A2 | 2/2006 |
| EP | 1652481 A2 | 5/2006 |
| EP | 1382303 B1 | 6/2006 |
| EP | 1045672 B1 | 8/2006 |
| EP | 1617768 B1 | 8/2006 |
| EP | 1702567 A2 | 9/2006 |
| EP | 1129665 B1 | 11/2006 |
| EP | 1256317 B1 | 12/2006 |
| EP | 1728473 A1 | 12/2006 |
| EP | 1728475 A2 | 12/2006 |
| EP | 1479346 B1 | 1/2007 |
| EP | 1484024 B1 | 1/2007 |
| EP | 1754445 A2 | 2/2007 |
| EP | 1759812 A1 | 3/2007 |
| EP | 1769756 A1 | 4/2007 |
| EP | 1769758 A1 | 4/2007 |
| EP | 1785097 A2 | 5/2007 |
| EP | 1790293 A2 | 5/2007 |
| EP | 1800610 A1 | 6/2007 |
| EP | 1300117 B1 | 8/2007 |
| EP | 1813199 A1 | 8/2007 |
| EP | 1813201 A1 | 8/2007 |
| EP | 1813203 A2 | 8/2007 |
| EP | 1813207 A1 | 8/2007 |
| EP | 1813209 A1 | 8/2007 |
| EP | 1839596 A1 | 10/2007 |
| EP | 1402821 B1 | 12/2007 |
| EP | 1872727 A1 | 1/2008 |
| EP | 1897502 A1 | 3/2008 |
| EP | 1702568 B1 | 7/2008 |
| EP | 1970014 A1 | 9/2008 |
| EP | 1980213 A2 | 10/2008 |
| EP | 1759645 B1 | 11/2008 |
| EP | 1693008 B1 | 12/2008 |
| EP | 2000102 A2 | 12/2008 |
| EP | 1749486 B1 | 3/2009 |
| EP | 2090256 A2 | 8/2009 |
| EP | 1813206 B1 | 4/2010 |
| EP | 1769754 B1 | 6/2010 |
| FR | 2765794 A | 1/1999 |
| GB | 939929 A | 10/1963 |
| GB | 1210522 A | 10/1970 |
| GB | 2336214 A | 10/1999 |
| JP | 6007357 A | 1/1994 |
| JP | 7051273 A | 2/1995 |
| JP | 8033641 A | 2/1996 |
| JP | 8229050 A | 9/1996 |
| JP | 2000287987 A | 10/2000 |
| JP | 2001286477 A | 10/2001 |
| JP | 2002369820 A | 12/2002 |
| JP | 2005505322 T | 2/2005 |
| JP | 2005103293 A | 4/2005 |
| RU | 2187249 C2 | 8/2002 |
| RU | 2225170 C2 | 3/2004 |
| SU | 1377053 A1 | 2/1988 |
| SU | 1561964 A1 | 5/1990 |
| SU | 1722476 A1 | 3/1992 |
| WO | WO 93/08755 A1 | 5/1993 |
| WO | WO 95/18572 A1 | 7/1995 |
| WO | WO 95/23557 A1 | 9/1995 |
| WO | WO 95/29639 A1 | 11/1995 |
| WO | WO 96/22055 A1 | 7/1996 |
| WO | WO 96/35464 A1 | 11/1996 |
| WO | WO 97/34533 A1 | 9/1997 |
| WO | WO 97/39688 A2 | 10/1997 |
| WO | WO 98/17180 A1 | 4/1998 |
| WO | WO 98/30153 A1 | 7/1998 |
| WO | WO 99/12483 A1 | 3/1999 |
| WO | WO 99/15086 A1 | 4/1999 |
| WO | WO 99/34744 A1 | 7/1999 |
| WO | WO 99/45849 A1 | 9/1999 |
| WO | WO 00/24322 A1 | 5/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/05702 A1 | 1/2001 |
| WO | WO 01/10482 A1 | 2/2001 |
| WO | WO 01/54594 A1 | 8/2001 |
| WO | WO 01/62158 A2 | 8/2001 |
| WO | WO 01/62162 A1 | 8/2001 |
| WO | WO 01/62164 A2 | 8/2001 |
| WO | WO 01/91646 A1 | 12/2001 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/30297 A2 | 4/2002 |
| WO | WO 02/32322 A2 | 4/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/020106 A2 | 3/2003 |
| WO | WO 03/020139 A2 | 3/2003 |
| WO | WO 2003/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094747 A1 | 11/2003 |
| WO | WO 2003/094746 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/047653 A2 | 6/2004 |
| WO | WO 2004/049956 A2 | 6/2004 |
| WO | WO 2004/086987 A1 | 10/2004 |
| WO | WO 2004/096057 A2 | 11/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/078892 A1 | 8/2005 |
| WO | WO 2005/096954 A2 | 10/2005 |
| WO | WO 2005/112808 A1 | 12/2005 |
| WO | WO 2005/115251 A2 | 12/2005 |
| WO | WO 2006/044490 A2 | 4/2006 |
| WO | WO 2006/044581 A2 | 4/2006 |
| WO | WO 2006/044810 A2 | 4/2006 |
| WO | WO 2006/083748 A1 | 8/2006 |
| WO | WO 2006/115958 A2 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |

(56) References Cited

FOREIGN PATENT DOCUMENTS

| WO | WO 2007/098220 A2 | 8/2007 |
|----|----|----|
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2008/039270 A1 | 4/2008 |
| WO | WO 2008/045383 A2 | 4/2008 |

OTHER PUBLICATIONS

Disclosed Anonymously, "Motor-Driven Surgical Stapler Improvements," Research Disclosure Database No. 526041, Published: Feb. 2008.

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

U.S. Appl. No. 11/821,277, filed Jun. 22, 2007.

U.S. Appl. No. 12/031,368, filed Feb. 14, 2008.

The Sodem Aseptic Battery Transfer Kit, Sodem Systems, 2000, 3 pages.

"Biomedical Coatings," Fort Wayne Metals, Research Products Corporation, obtained online at www.fwmetals.com on Jun. 21, 2010 (1 page).

\* cited by examiner

LAPAROSCOPIC TISSUE THICKNESS AND CLAMP LOAD MEASURING DEVICES

FIELD OF THE INVENTION

The present invention relates in general to laparoscopic and endoscopic surgical instruments and, more particularly, to endoscopic surgical devices and grasping devices configured to enable the surgeon to measure tissue thickness and clamping loads.

BACKGROUND OF THE INVENTION

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument commonly includes a plurality of reciprocating wedges which, when driven distally, pass through openings in the staple cartridge and engage drivers supporting the staples to effect the firing of the staples toward the anvil.

When using an endocutter during endoscopic surgery, it is often difficult for the surgeon to determine the thickness of the tissue that they are about to transect. The thickness of the tissue determines the type of cartridge/staple they need in order to properly seal the transection. Often times, the surgeon must make the thickness determination based upon their visual observations of the tissue on a monitor or, if possible, they use their hands to feel the thickness of the tissue.

Another type of device that is commonly employed during laparoscopic surgery is known as a grasper. Such graspers typically have a pair of opposing jaws that are used to grasp tissue or portions of other surgical instruments during the surgical procedure. Such grasping devices, however, also lack means for determining tissue thicknesses. In addition, the jaw arrangements employed by such graspers are often ill-suited to effectively grip and manipulate other surgical instruments used during the operation.

Consequently, a significant need exists for a laparoscopic device that would permit a surgeon to accurately and repeatably measure tissue thickness to enable the surgeon to select a proper staple cartridge to perform a transection. There is a further need for graspers that have tissue thickness measuring capabilities and jaws designed to effectively grasp other surgical instruments therebetween.

The foregoing discussion is intended only to illustrate some of the shortcomings present in the field of the invention at the time, and should not be taken as a disavowal of claim scope.

SUMMARY

In one aspect of the invention, there is provided a surgical instrument that comprises a pair of opposing jaws, wherein at least one jaw is selectively movable relative to the other jaw in response to opening and closing motions applied thereto for selectively clamping tissue therebetween. An output generator is associated with the pair of opposing jaws and is capable of generating tissue thickness data or indicia that represents a thickness of the tissue that is clamped between the pair of opposing jaws. The surgical instrument may further include a display for displaying the tissue thickness data or indicia thereon. In various embodiments, the tissue thickness data or indicia may be displayed on a display located on the surgical instrument itself or it may be displayed on a display located remote from the surgical instrument.

In another general aspect of various embodiments of the present invention there is provided a surgical instrument that comprises a handle assembly and an end effector for performing a surgical operation. The end effector is coupled to the handle assembly and has opposed jaw members for selectively clamping tissue therebetween in response to opening and closing motions applied thereto. A closure drive is supported by the handle assembly and is configured to generate the opening and closing motions for selective application to the end effector. The end effector may include at least one signal generator for generating signals corresponding to a thickness of the tissue clamped between the opposed jaw members. The instrument may further include a signal processor for receiving said signals from the signal generator and calculating the thickness of the tissue. In addition, a display communicates with the signal processor for displaying the tissue thickness thereon.

In still another general aspect of various embodiments of the present invention there is provided a jaw arrangement for a surgical instrument that comprises a first jaw that is operably coupleable to the surgical instrument and has a distal end and a first clamping face and at least one first nodule that is formed on the first clamping face. The arrangement further includes a second jaw that has a distal end and a second clamping face. At least one second nodule is formed on the second clamping face. The second jaw is operably coupleable to the surgical instrument relative to the first jaw such that the first and second distal ends of the first and second jaws, respectively may be selectively moved toward and away from each other upon application of open and closing motions to at least one of the first and second jaws from the surgical instrument such that as the first and second distal ends are moved towards each other, the first and second distal ends and the first and second nodules cooperate to define a cradle area therebetween sized to grippingly support therein an object having a specific cross-sectional shape.

In another aspect of the present invention, there is provided a surgical instrument that may comprise a handle assembly and a pair of opposing jaws that are operably coupled to the handle assembly. The opposing jaws may be selectively movable between open and closed positions for clamping tissue therebetween. The surgical instrument may further include a closure drive that is operably supported by the handle assembly for selectively applying opening and closing motions to the pair of opposing jaws. An output generator may cooperate with the closure drive to display reference indicia that corresponds to a thickness of the tissue clamped between the pair of opposing jaws.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain various principles of the present invention.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

The present invention generally relates to methods and devices for measuring the thickness of tissue to be transected or otherwise manipulated during endoscopic and laparoscopic procedures. In one exemplary embodiment, the measuring device can be employed in connection with an endocutter for transecting and stapling tissue. Such endocutters typically include an end effector with opposing jaws that are adapted to receive the target tissue therebetween. As will be described in connection with one exemplary embodiment, the end effector is attached to a handle assembly by an elongated shaft assembly. The handle assembly is equipped with a closure trigger that enables the surgeon to selectively open and close the end effector jaws. The end effector is also equipped with a firing drive system for driving a knife through the staple cartridge and clamped tissue while also driving the staples housed within the staple cartridge into forming contact with an anvil. Other exemplary embodiments comprise a surgical device that has a pair of opposed jaws for simply manipulating and grasping tissue, other surgical instruments, etc.

As the present Detailed Description proceeds, a person of ordinary skill in the art will appreciate that the surgical instruments described herein can have a variety of configurations, and that one or more of the various tissue measurement features of the various embodiments of the present invention disclosed herein can be successfully used in a variety of different grasping device/end effectors known in the art for grasping/manipulating tissue or other objects. Thus, the term "surgical instrument" as used herein is intended to include any device that has opposed movable jaws that come together to grasp, clamp, cut, dissect, staple, etc.

Figure 1:
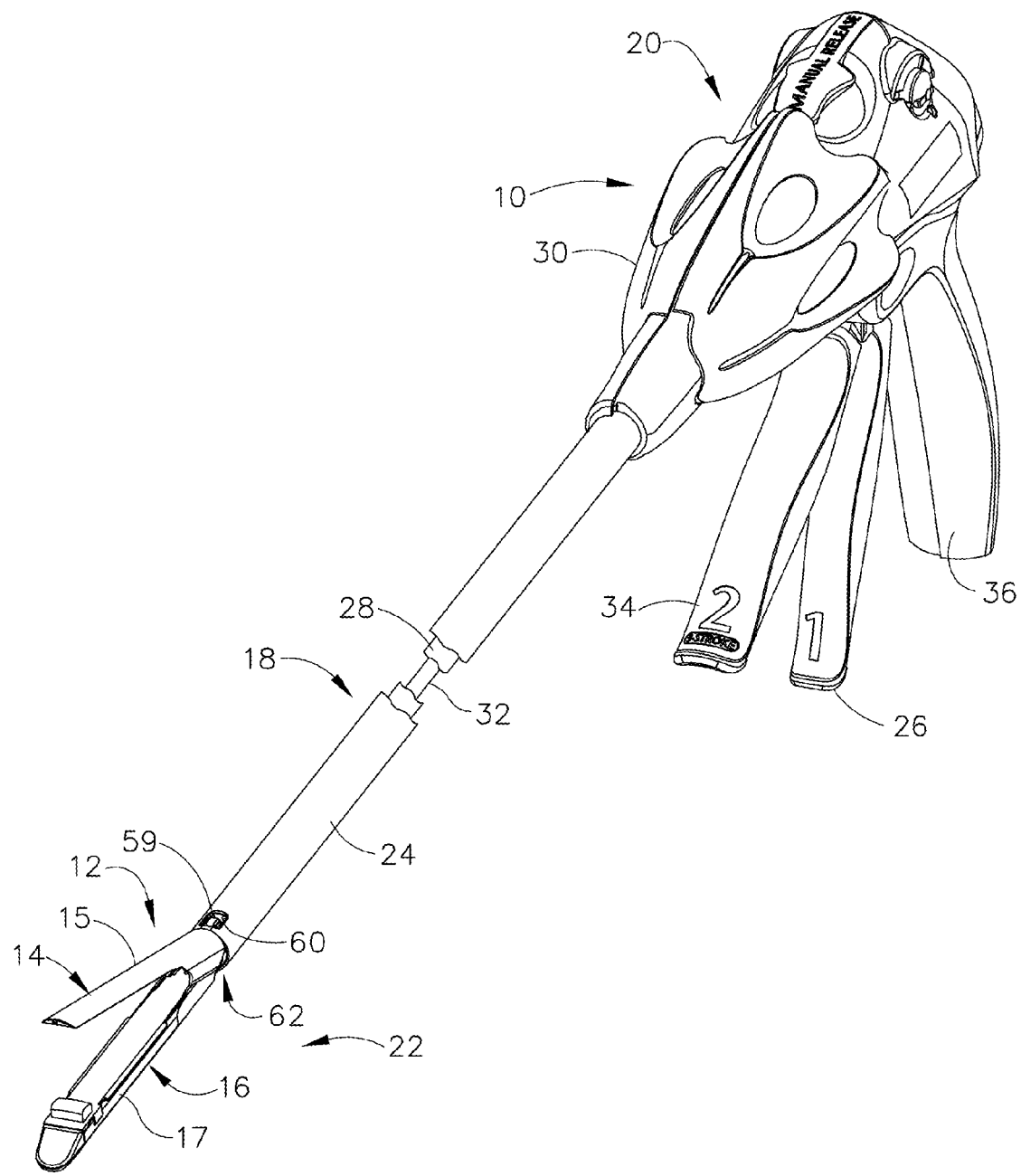
FIG. 1 is a perspective view of a surgical stapling and severing instrument of various embodiments of the present invention.
Figure 2:
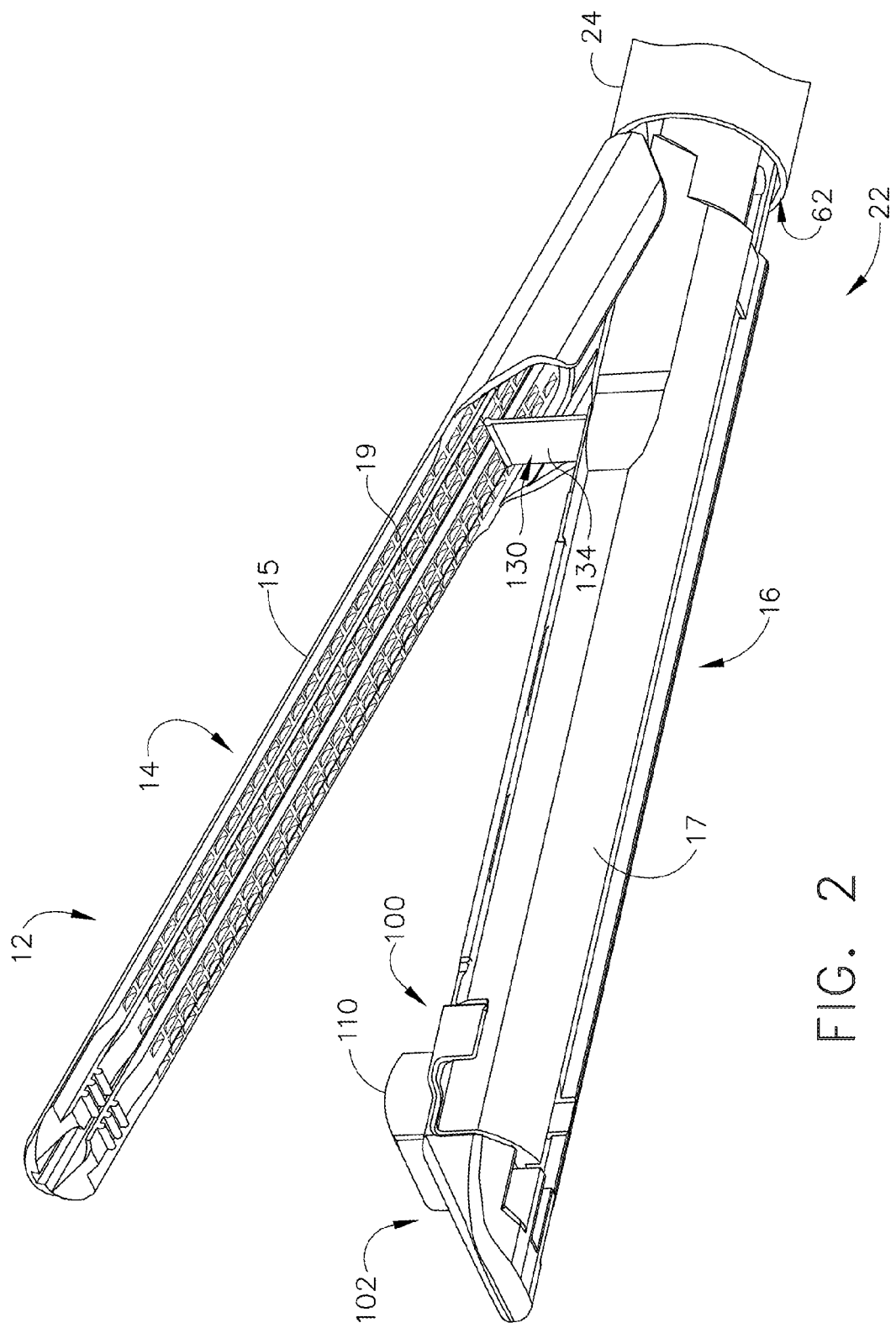
FIG. 2 is a left side perspective view of an end effector embodiment of the present invention.

Turning to the Drawings, wherein like numerals denote like components throughout the several views, FIGS. 1 and 2 depict a surgical stapling and severing instrument 10 that is capable of practicing various unique benefits of the present invention. The surgical stapling and severing instrument 10 incorporates an end effector 12 that has a first jaw 14 and a second jaw 16. In various embodiments, the second jaw 16 may comprise elongate channel 17 and the first jaw may comprise an anvil 15 that is pivotally attached to the elongate channel 17, forming opposing jaws for clamping tissue to be severed and stapled. Those of ordinary skill in the art will understand that the exemplary endocutter embodiment depicted in the Figures comprises one endocutter version with which various embodiments of the present invention may be successfully employed. However, various embodiments of the present invention may be used in connection with a variety of different endocutter instruments. For example, various embodiments of the present invention may be used in connection with those surgical instruments disclosed in U.S. Pat. No. 6,978,921 to Shelton, I V et al., entitled Surgical Stapling Instrument Incorporating an E-Beam Firing Mechanism, the disclosure of which is herein incorporated by reference.

As can be seen in FIG. 1, the end effector 12 may be coupled to a handle assembly 20 by an elongate shaft assembly 18. An implement portion 22, formed by the end effector 12 and shaft assembly 18, may be advantageously sized for insertion through a trocar or small laparoscopic opening to perform an endoscopic surgical procedure while being controlled by a surgeon grasping the handle assembly 20. The handle assembly 20 may include features that allow separate closure motions and firing motions, lockouts to prevent inadvertent or ill-advised firing of the end effector, as well as enabling multiple firing strokes to effect firing (i.e., severing and stapling) of the end effector 12 while indicating the degree of firing to the surgeon.

To these ends, a closure tube 24 of the shaft assembly 18 may be coupled between a closure trigger 26 (FIG. 1) and the anvil 15 to cause closure of the end effector 12. Within the closure tube 24, a frame 28 may be coupled between the elongate channel 17 and the handle assembly 20 to longitudinally position and support the end effector 12. A rotation knob 30 may be coupled with the frame 28, and both elements may be rotatably coupled to the handle assembly 20. Thus, the surgeon can rotate the end effector 12 by turning the rotation knob 30 which causes rotation of the closure tube 24. The frame 28 extends through the closure tube 24 along with a firing rod 32 which is positioned for longitudinal movement and is operably coupled to a firing trigger 34. In the embodiment depicted in FIG. 1, the closure trigger 26 is distal to a pistol grip 36 of the handle assembly 20 with the firing trigger 34 distal to both the pistol grip 36 and closure trigger 26.

It will be appreciated that the terms "proximal" and "distal" are used herein with reference to a clinician gripping a handle of an instrument. Thus, the end effector 12 is distal with respect to the more proximal handle assembly 20. Analogous terms such as "front" and "back" similarly correspond respectively to distal and proximal. It will be further appreciated that for convenience and clarity, spatial terms such as "vertical", "horizontal", "up" and "down" are used herein with respect to the drawings. However, surgical instruments are used in many orientations and positions, and these terms are not intended to be limiting and absolute.

The present invention is being discussed in terms of endoscopic procedures and apparatus. However, use herein of terms such as "endoscopic", should not be construed to limit the present invention to a surgical stapling and severing instrument for use only in conjunction with an endoscopic tube (i.e., trocar). On the contrary, it is believed that the present invention may find use in any procedure where access is limited to a small incision, including but not limited to laparoscopic procedures, as well as open procedures.

Figure 3:
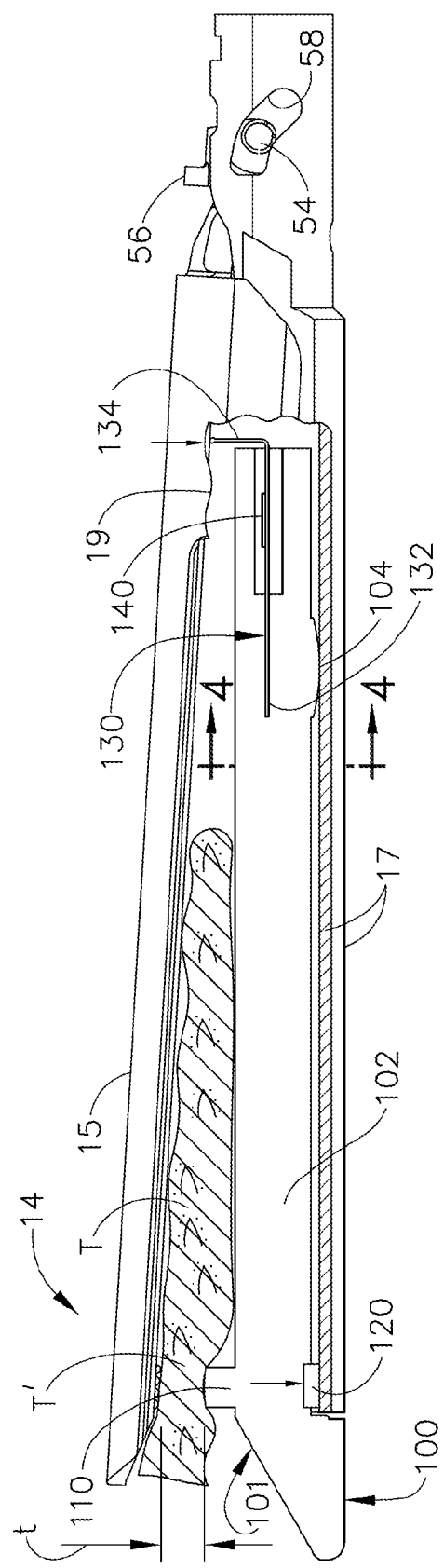
FIG. 3 is a cross-sectional view of the end effector of FIG. 2 with a portion of tissue clamped between the anvil and tissue measurement cartridge.
Figure 4:
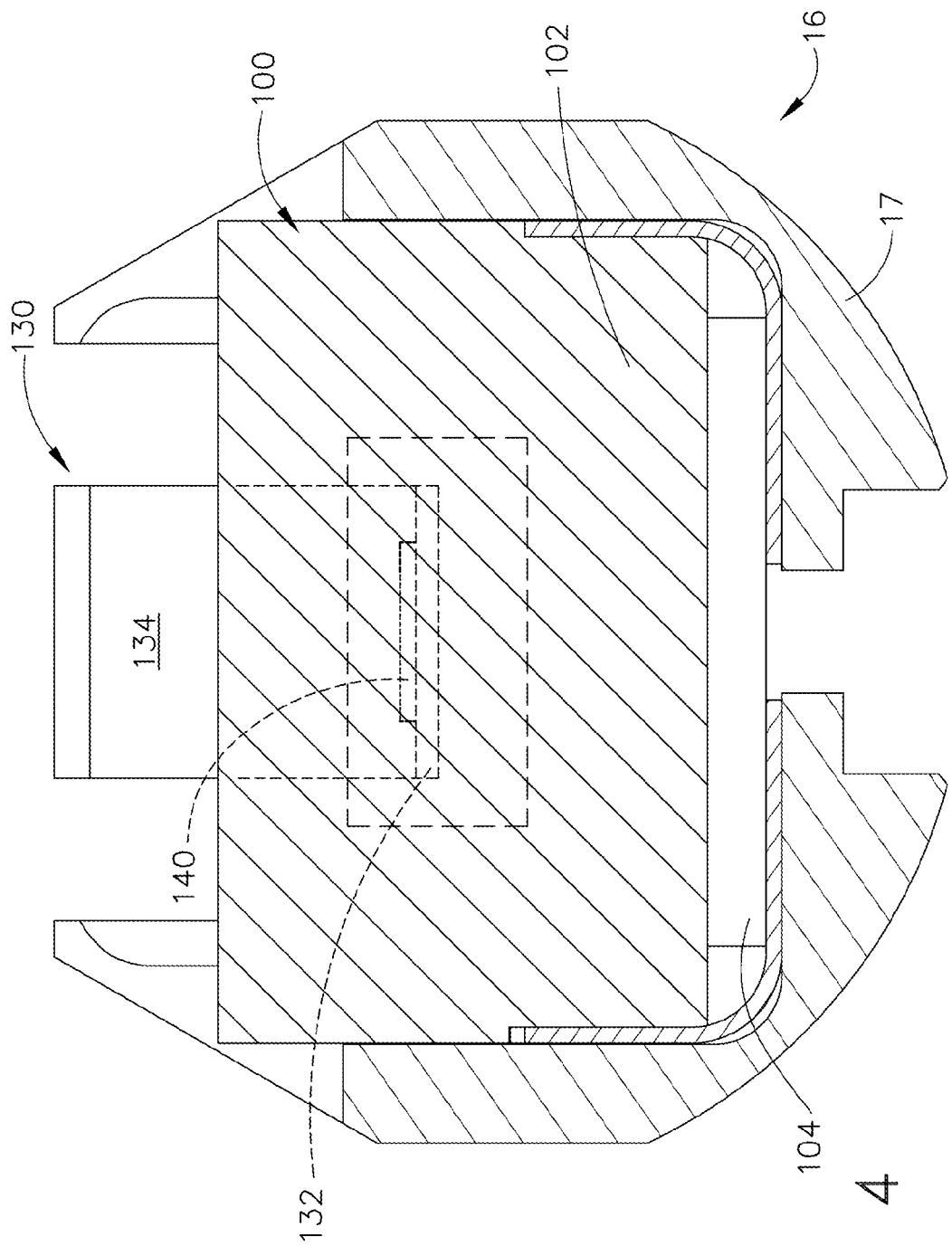
FIG. 4 is a cross-sectional view of the end effector of FIG. 3 taken along line 4-4 in FIG. 3.

With particular reference to FIG. 3, the anvil 15 is pivotally coupled to the elongate channel 17 by a pair of laterally projecting anvil pivot pins 54 that are proximal to a vertically projecting anvil feature 56 (FIG. 4). The anvil pivot pins 54 translate within kidney shaped openings 58 in the elongate channel 17 to open and close anvil 15 relative to elongate channel 17. The anvil feature 56 engages a tab 59 (FIG. 1) extending inwardly in a tab aperture 60 on a distal end 62 of the closure tube 24. Thus, when the closure tube 24 moves proximally from its open position, the tab 59 of the closure tube 24 draws the anvil feature 56 proximally, and the anvil pivot pins 54 follow the kidney shaped openings 58 of the elongate channel 17 causing the anvil 15 to simultaneously translate proximally and rotate upward to the open position. When the closure tube 24 moves distally, the tab 59 in the tab aperture 60 releases from the anvil feature 56 and the distal edge 64 pushes on the anvil face 50, closing the anvil 15.

It should be appreciated that, although a nonarticulating shaft assembly 18 is illustrated herein, applications of the present invention may include instruments capable of articulation, such as those described in three commonly owned U.S. patents and two commonly owned U.S. patent applications, the disclosure of each being hereby incorporated by reference in their entirety: (1) U.S. Pat. No. 7,111,769 to Kenneth S. Wales, Douglas B. Hoffman, Frederick E. Shelton I V, and Jeffrey S. Swayze, issued Sep. 26, 2006, entitled "Surgical instrument Incorporating An Articulation Mechanism Having Rotation About the Longitudinal Axis"; (2) U.S. Pat. No. 6,981,628 to Kenneth S. Wales, issued Jan. 3, 2006, entitled "Surgical Instrument With A Lateral-Moving Articulation Control"; (3) U.S. Pat. No. 7,055,731 to Frederick E. Shelton I V, Michael E. Setser, William B. Weisenburgh II, issued Jun. 6, 2006 entitled "Surgical Stapling Instrument Incorporating A Tapered Firing Bar For Increased Flexibility Around The Articulation Joint"; (4) U.S. Patent Publication No. 2005/0006429 entitled "Surgical Stapling Instrument Having Articulation Joint Support Plates For Supporting A Firing Bar", Ser. No. 10/615,971, to Kenneth S. Wales and Joseph Charles Hueil, filed 9 Jul. 2003; and (5) U.S. patent application entitled "Surgical Stapling Instrument Incorporating An Articulation Joint For a Firing Bar Track", Ser. No. 10/615,962, to Brian J. Hemmelgam, filed 9 Jul. 2003. Those of ordinary skill in the art will readily understand, however, that the unique and novel aspects of various features of the present invention may be employed in connection with still other types of articulating surgical instruments without departing from the spirit and scope of the present invention.

With reference to FIGS. 2 and 3, the elongate channel 17 is configured to removably receive a thickness measurement cartridge 100 therein. Thickness measurement cartridge 100 may resemble a conventional staple cartridge. However, thickness measurement cartridge 100 lacks the staples and staple firing drivers and may also differ from a conventional staple cartridge in at least the manners described below. In particular, the body portion 102 of the thickness measurement cartridge 100 may have an upstanding clamping nodule 110 that is formed on a distal end 101 of the cartridge 100. The clamping nodule 110 may be so oriented on the distal end 101 of the cartridge 100 such that when the cartridge 100 is installed in the elongate channel 17, the clamping nodule 110 is located over a first conventional strain gauge 120 that is mounted within the elongate channel 17. The purpose of the first strain gauge 120 will be discussed in further detail below.

Figure 5:
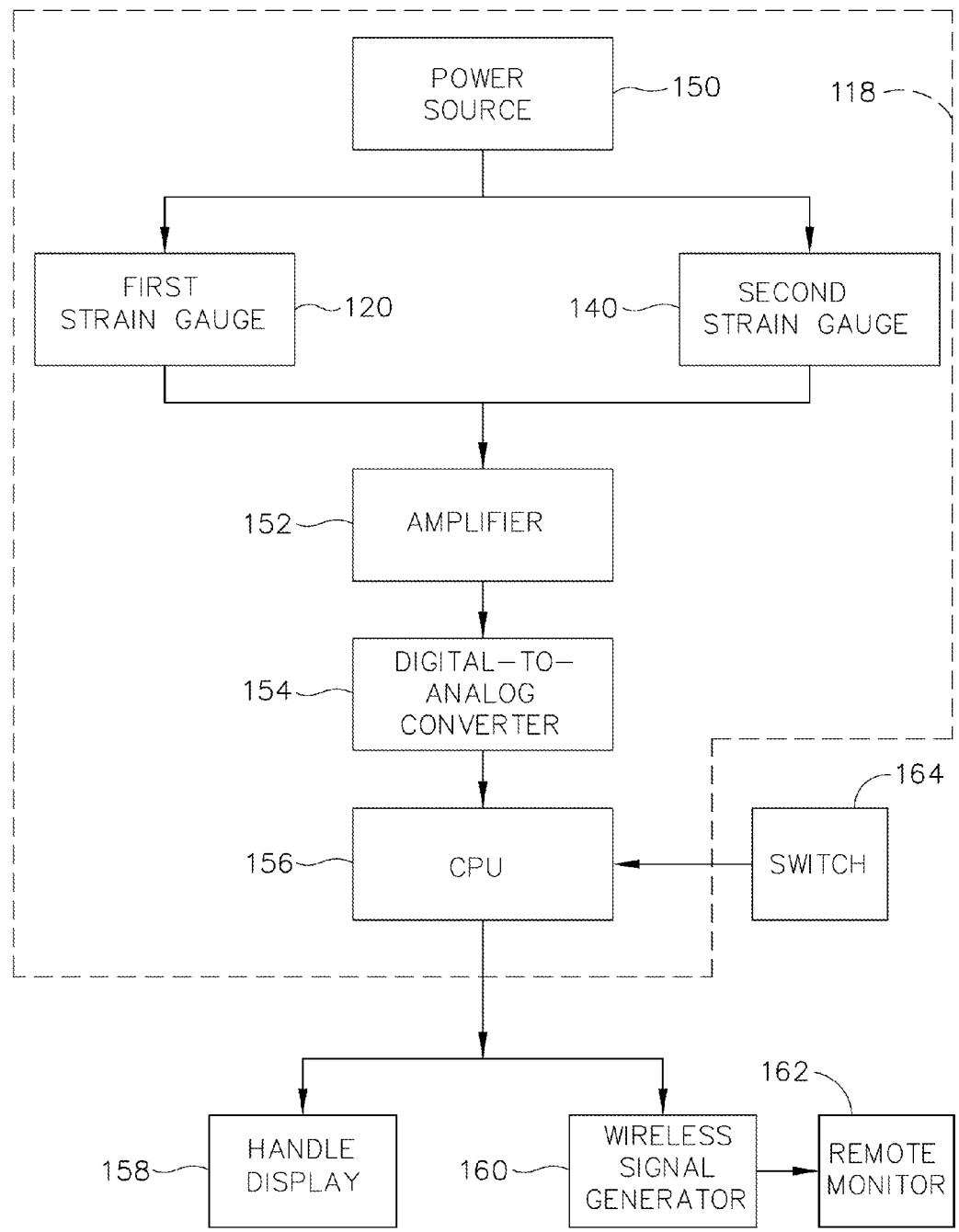
FIG. 5 is a schematic diagram of a strain gauge and operating system arrangement of various embodiments of the present invention.

As can also be seen in FIGS. 2 and 3, the thickness measurement cartridge 100 may also include a thickness or anvil probe 130 that is mounted within the cartridge body 102. More specifically, as can be seen in FIG. 3, the anvil probe 130 may include a first portion 132 that is mounted within the cartridge body 102 and a second deflectable portion 134 that protrudes upwardly from the cartridge body 102 for contact with the underside 19 of the anvil 15. The anvil probe 130 may be fabricated from metal or other suitable material and may be associated with a second strain gauge 140 that is mounted in the cartridge body 102. The first and second strain gauges 120, 140 may each be coupled to a battery or other source of electrical power 150, an amplifier 152, a digital-to-analog converter 154, a conventional central processing unit "CPU" 156, and a display unit 158. The battery 150, amplifier 152, the converter 154, CPU 156 and display unit 158 may be housed within the handle assembly 20. Each strain gauge may have its own amplifier. The first and second strain gauges 120, 140 and the source of electrical power 150, amplifier, 152, converter 154 and CPU 156 may collectively form an output generator generally designated as 118. In alternative embodiments, the CPU 156 may also be coupled to a wireless signal generator 160 that transmits the thickness data to a remote (i.e., not supported by the handle assembly 20) monitor 162. See FIG. 5. The measurement cartridge 100 may be formed with a pin and socket connection (not shown) to facilitate electrical communication between the second strain gauge 140 and conductors in the elongate channel 17 that extend through the shaft 18 and are ultimately coupled to the CPU 156 and/or source of electrical power 150.

Operation of a thickness measurement cartridge 100 of various embodiments of the present invention will now be described with reference to FIGS. 1, 3, 4, and 5. Prior to installing a conventional staple cartridge into the elongate channel 17 of the instrument 10, the surgeon may first install the thickness measurement cartridge 100 into the elongate channel 17. The thickness measurement cartridge 100 may be fabricated with retention features that are commonly found on conventional staple cartridges to removably retain the thickness measurement cartridge 100 within the elongate channel 17. When installed, a pin and socket connector or other arrangement may connect the second strain gauge 140 to the source of electrical power 150 and amplifier 152.

In laparoscopic and endoscopic surgical procedures, a small incision or puncture is made in the patient's body to provide access for a tube or cannula device. Once extended into the patient's body, the cannula allows insertion of various surgical instruments to perform the surgery. After the surgeon has installed the thickness measurement cartridge 100 in the elongate channel 17, the surgeon may then insert the implement 22 through the cannula (not shown) so that a portion T' of the tissue "T" to be transected is positioned between the underside 19 of the anvil 15 and the measurement cartridge 100. See FIG. 3. The surgeon then moves the closure trigger 26 towards the pistol grip 36 to move the closure tube 24 in a known manner to pivot the anvil 15 in a closing direction. As the anvil 15 is pivoted in the closing direction, a portion of the tissue "T" to be transected is clamped between the underside 19 of the anvil 15 and the nodule 110. As can be most particularly seen in FIGS. 3 and 4, a pivot protrusion 104 may be formed on the underside of the cartridge body 102 to rest on the bottom of the elongate cartridge 17 to thereby enable the cartridge body 102 to pivot thereon.

As the anvil 15 begins to clamp the tissue "T" between the underside 19 of the anvil 15 and the nodule 110, the first strain gauge 120 is placed under load and may act as a resistor, such that, as the load that is applied to the first strain gauge 120, the first strain gauge 120 either increases or decreases the amount of resistance to the electricity supplied to it from the source of electrical power 150. The amplifier 152 amplifies the signal from the first strain gauge 120 and feeds the amplified signal into the digital-to-analog converter 154 that changes raw current into digital data. The digital data is then sent to the CPU 156 which interprets the digital signal and mathematically transforms the data into a first amount of strain or load which is displayed by the handle display 158 and/or is sent to a wireless signal generator 160 which wirelessly transmits the data to a remote monitor 162. See FIG. 5. The surgeon continues to close the anvil 15 until the display indicates that the tissue "T" within the first and second jaws 14, 16 has been clamped under a predetermined amount of clamping load. For example, the predetermined amount of clamping load or force may be eight grams. Such force may not, for example, damage the tissue "T", but may provide a reference point for repeatability purposes.

As the anvil 15 is being closed, the undersurface 19 of the anvil 15 starts to impart a load onto the anvil probe 134 which is conveyed to the second strain gauge 140 located in the cartridge 100. The amplifier 152 amplifies the output signal from the second strain gauge 140 and feeds the amplified signal into the digital-to-analog converter 154 that changes raw current into digital data. The digital data is then transmitted to the CPU 156 which interprets the digital signal and mathematically transforms the data into a tissue thickness that is displayed on the handle display 158 and/or is transmitted to the wireless signal generator 160 for sending to a remote monitor 162. After the surgeon has determined the thickness "t" of the tissue to be transected, the implement portion 22 is withdrawn to enable the thickness measurement cartridge 100 to be replaced with the appropriate staple cartridge. The measurement cartridge 100 may then be resterilized for the next procedure or simply disposed of.

Figure 6:
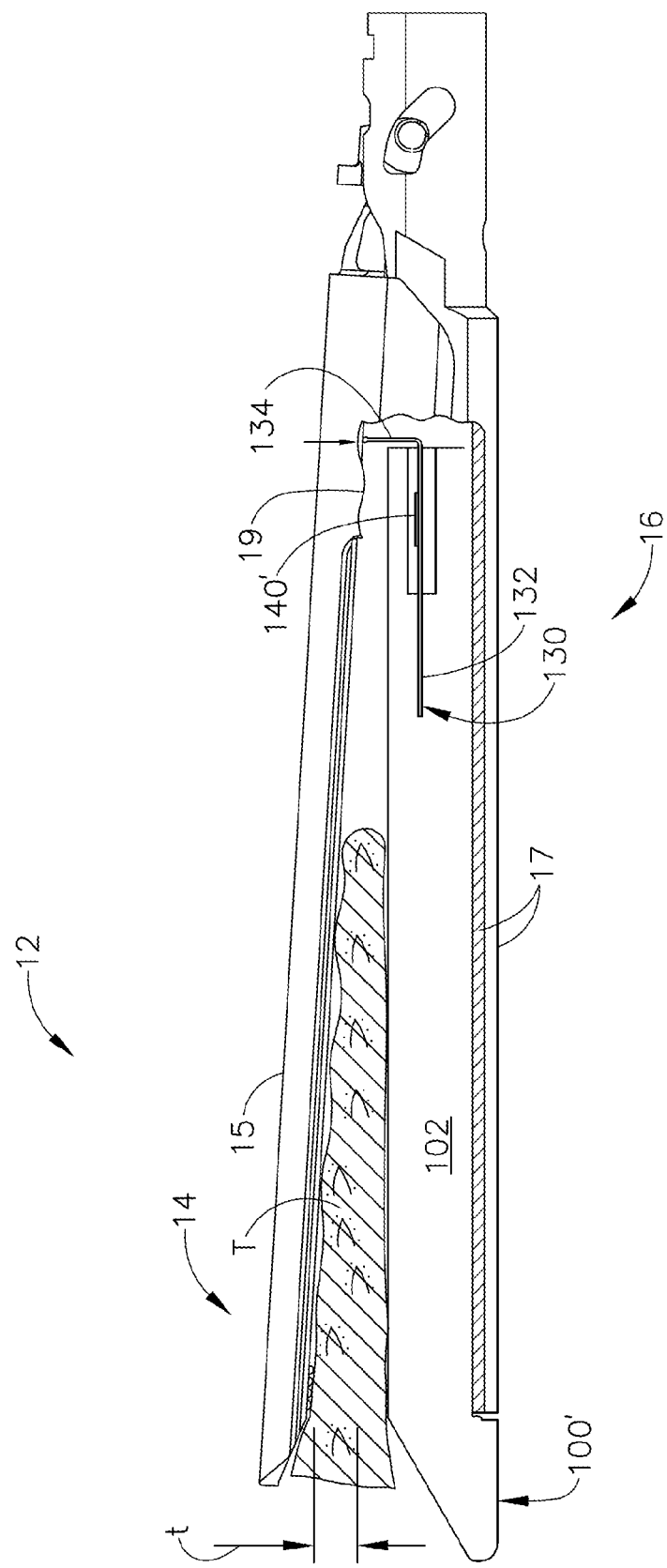
FIG. 6 is a cross-sectional view of another end effector embodiment of the present invention with tissue clamped between the anvil and the tissue measurement cartridge.
Figure 7:
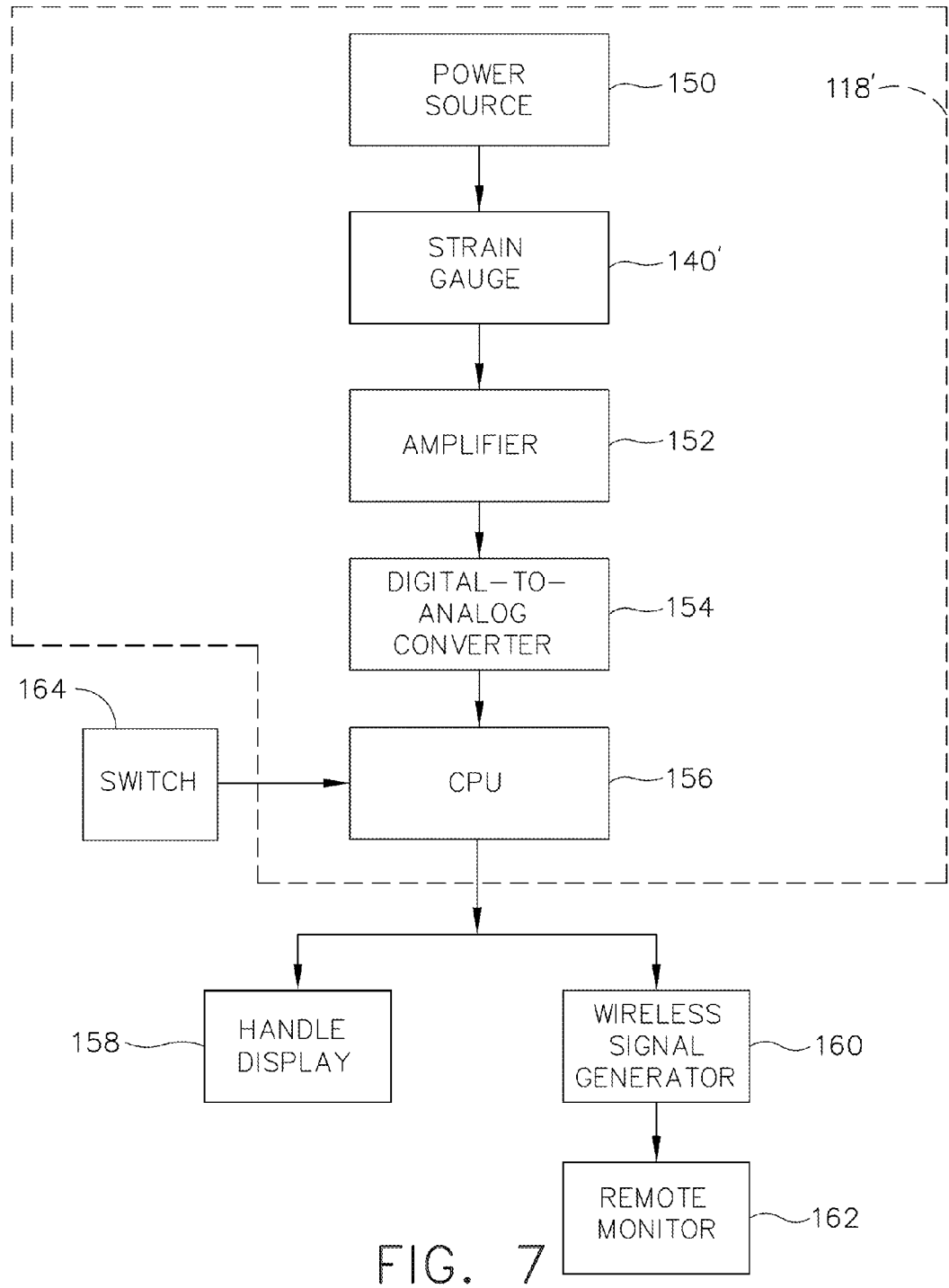
FIG. 7 is a schematic diagram of a strain gauge and operating system arrangement of another embodiment of the present invention.

In an alternative embodiment as depicted in FIGS. 6 and 7, the measurement cartridge 100' lacks the nodule and the first strain gauge that was included in the measurement cartridge 100 as described above. This embodiment may only be equipped with a strain gauge 140'. Thus, in this embodiment, the output generator 118' may comprise the source of electrical power 150, the strain gauge 140', the amplifier 152, the converter 154, and the CPU 156. Otherwise, cartridge 100' may be substantially identical to cartridge 100. FIG. 7 is a schematic drawing of the interface between the strain gauge 140' and the CPU 156. In this embodiment, the CPU 156 employs an algorithm that compares the strain values over time and waits until the strain is no longer changing within a desired delta, before it displays the final load reading or calculated tissue thickness "t" on the display. In addition, a switch 164 (mechanically or electrically activated) could be associated with the clamping trigger 26 for detecting the position of the clamping trigger 26. The switch 164 may communicate with the CPU 156 such that the CPU 156 would not start to process the strain loads until the clamping trigger 26 reached a predetermined position.

FIGS. 8-12 illustrate another surgical instrument 300 in the form of a grasper 302 that may employ various unique and novel features of various embodiments of the present invention. Such graspers 302 are known in the art and, therefore, the known features thereof, will not be discussed in great detail herein beyond what may be needed to fully understand and appreciate various embodiments of the subject invention. Examples of such devices are disclosed in U.S. Pat. No. 6,117,158 to Measamer et al. and U.S. Pat. No. 5,735,874 to Measamer et al., the disclosures of which are herein incorporated by reference.

Figure 8:
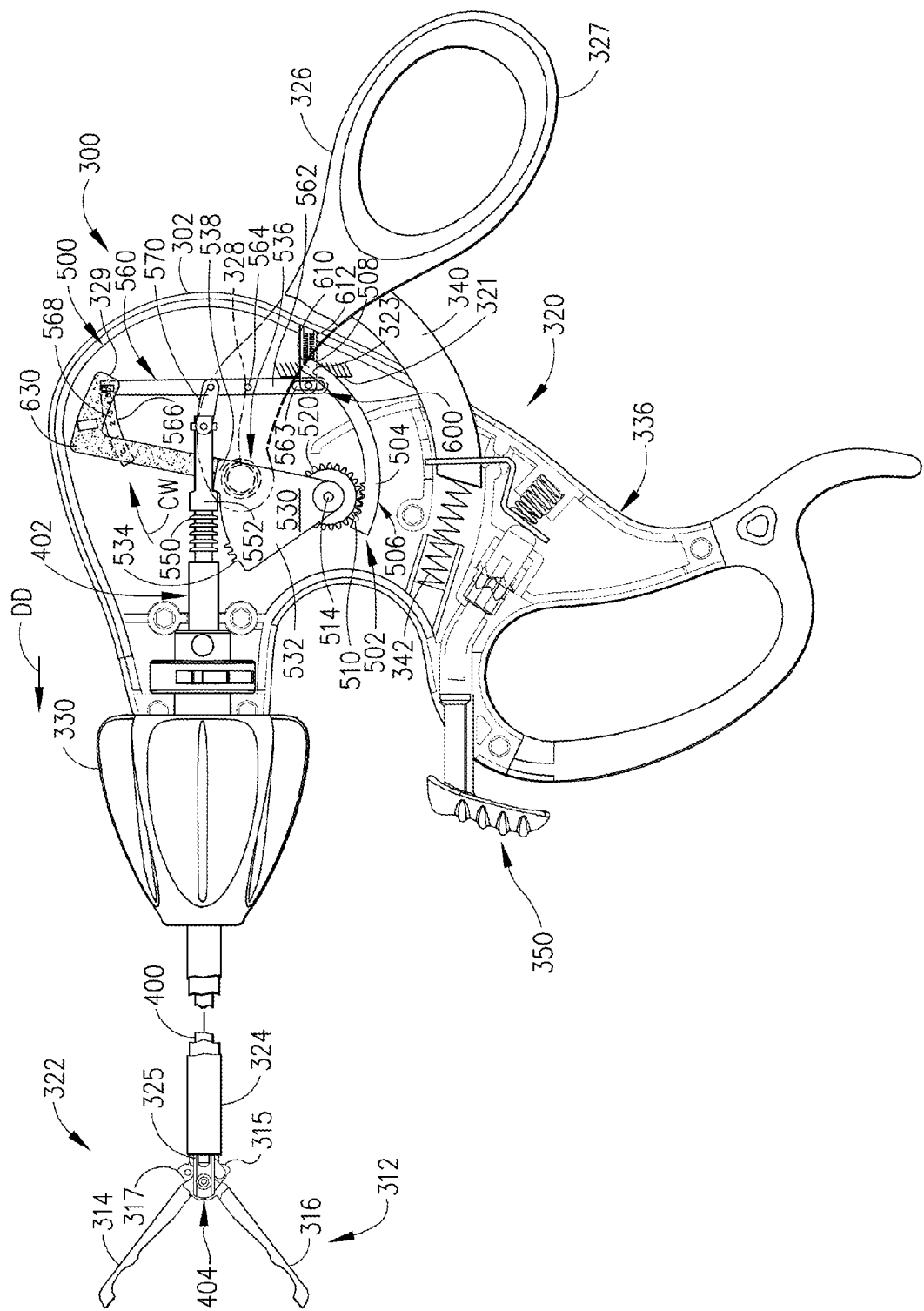
FIG. 8 is a side elevational view of a grasper embodiment of the present invention with the left hand side of the handle casing removed to show the various components supported within the handle assembly.

As can be seen in FIG. 8, the grasper 302 includes an end effector 312 that has a first jaw 314 and a second jaw 316 that are operably mounted to a grasper rod 400 that protrudes distally from a handle assembly 320. As is known, a proximal portion 402 of the grasper rod 400 may be rotatably supported within the handle assembly 320 and coupled to a rotation knob 330 rotatably supported on the handle assembly 320. Such arrangement permits the surgeon to rotate the grasper rod 400 (and jaws 314, 316) relative to the handle assembly 320. As can also be seen in FIG. 8, the grasper rod 400 extends through a closure tube 324 that also protrudes from the handle assembly 320.

As is known in the art, as the jaws 314 and 316 are pivotally coupled to a distal end 404 of the grasper rod 400 and may be retained in the open position illustrated in FIG. 8 by a spring arrangement (not shown). The jaws 314 and 316 are caused to close when their respective proximal ends 315, 317 are brought into contact with a distal end 325 of the closure tube 324 as the grasper rod 400 is drawn in the proximal direction in response to the actuation of a closure trigger 326 attached to the handle assembly 320. As can be seen in FIG. 8, the closure trigger 326 is pivotally mounted on a pivot rod 328 for selective pivotal travel therearound. The closure trigger 326 has an arcuate follower arm 340 attached thereto that is constrained to pivot along an arcuate path within the handle assembly 320 as the closure trigger 326 is pivoted between the open position shown in FIG. 8 and a closed position wherein the proximal end 327 of the pivot trigger 326 is substantially adjacent to a grip portion 336 of the handle assembly 330. Supported within the handle assembly 320 is a closure spring 342 that is arranged to engage the distal end of the follower arm 340 to bias the closure trigger 326 in the open position. In various embodiments, the grasper 320 may further include a locking trigger assembly 350 for locking the closure trigger 326 and ultimately the jaws 314, 316 in a specific clamping position. The construction and operation of such locking trigger assembly 350 is known in the art and therefore will not be described in detail herein.

As can be seen in FIG. 8, the grasper 302 is provided with an output generator generally designated as 500. In various embodiments, the output generator 500 may include a first gear 502 in the form of an arcuate arm 504 that has a series of gear teeth 510 formed on a distal end 506 thereof. A proximal end 508 is attached to the closure trigger 326. The gear teeth 510 are arranged in meshing engagement with the teeth of a second or closure gear 520 which is nonrotatably coupled to a bell crank 530. The second gear 520 may be rotatably supported on a second pivot rod 514 within the handle housing 320. As can be seen in FIG. 8, a distal end 532 of the bell crank 530 has a series of crank teeth 534 formed thereon and a retainer tab 538 formed on a proximal end 536 thereof. Thus, by pivoting the closure trigger 326 toward the grip portion 330, the bell crank 530 is rotated in a clockwise direction "CW" as shown in FIG. 8.

Figure 9:
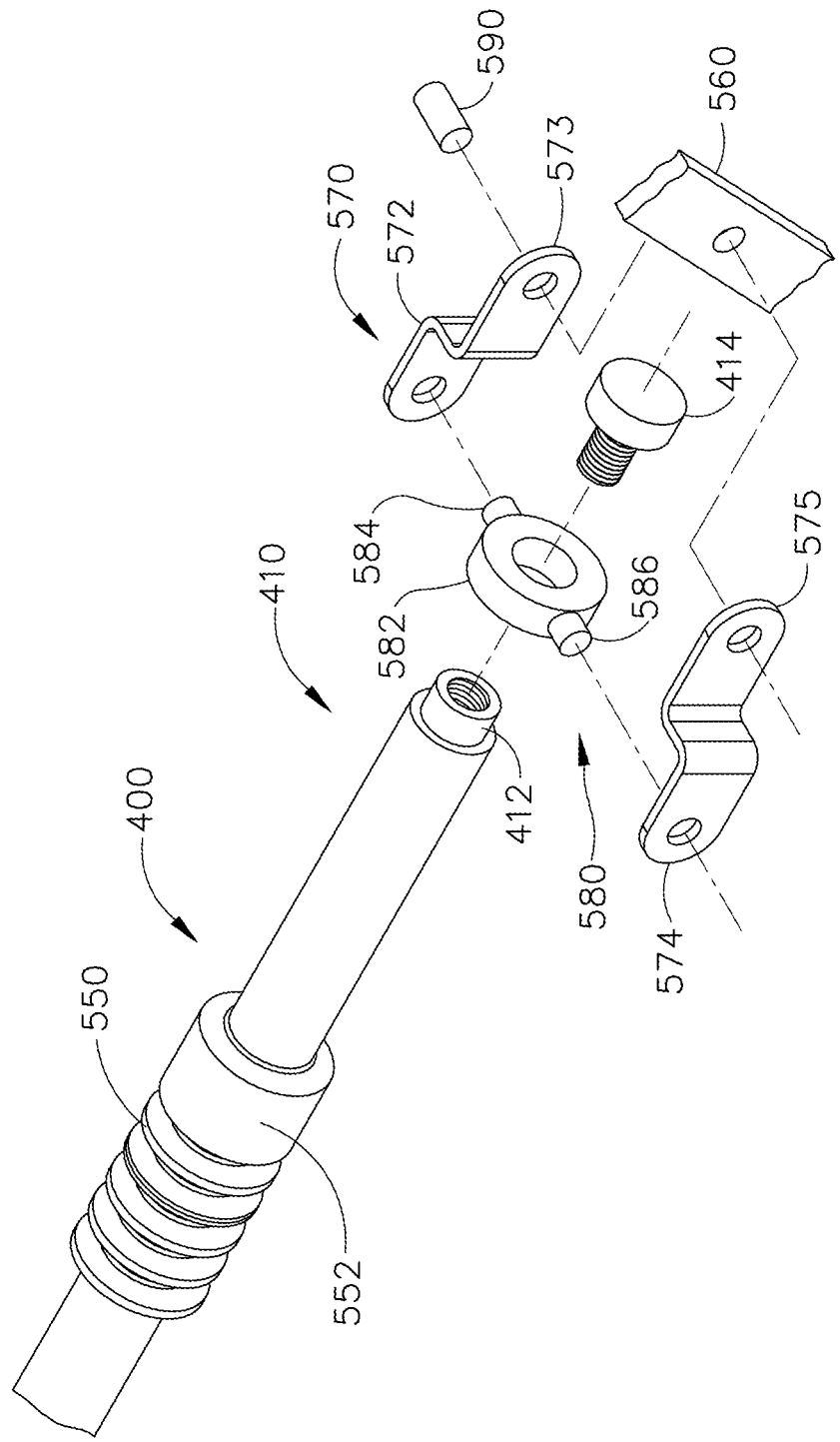
FIG. 9 is an exploded assembly view of a portion of the grasper rod arrangement employed in the grasper embodiment depicted in FIG. 8.

Also in this embodiment, a series of rings 550 may be formed on a portion of the grasper rod 400. The rings 550 are located on the grasper rod 400 for selective engagement with the crank teeth 534. A lug 552 is also formed adjacent the proximal-most ring 550. As can be seen in FIGS. 8 and 9, the proximal end 410 of the grasper rod 400 may be attached to a reference scale arm 560 by means of a linkage arm assembly 570. As was discussed above, it may be desirable for the surgeon to be able rotate the grasper rod 400 relative to the handle assembly 320 to facilitate accurate positioning of the jaws 314 and 316. Thus, in various embodiments, the proximal end 410 of the grasper rod 400 may be attached to the linkage arm assembly by a gimble-like joint assembly, generally designated as 580. As shown in FIG. 9, the gimble-like joint assembly 580 may include a collar 582 that has two circumferentially opposed pivot pins 584, 586 protruding therefrom. The collar 584 is received on a shoulder portion 412 of the grasper rod 400 and retained thereon by a screw 414 that threadably engages the proximal end 410 of the grasper rod 400 as shown. Those of ordinary skill in the art will understand that such arrangement serves to permit the grasper rod 400 to freely rotate within the collar 582 while being attached thereto.

As can also be seen in FIG. 9, the linkage arm assembly 570 may comprise a right linkage arm 572 that is pivotally attached to the right pivot pin 584 and a left linkage arm 574 that is attached to the left pivot pin 586. The proximal end 573 of the right linkage arm 572 and the proximal end 575 of the left linkage arm 574 may be pivotally attached to the scale arm 560 by a pivot pin 590. Thus, such arrangement enables grasper rod 400 to be linked to the scale arm 560 while permitting free rotation of the grasper rod 400 relative thereto. In various embodiments, the lower end 562 of the scale arm 560 may be pivotally coupled to handle case 320 by a pivot pin 564 to enable the scale arm 560 to pivot in sync with the grasper rod 400.

As can be seen in FIG. 8, the lower portion 562 of the scale arm 560 may also be attached to a load applying assembly 600. In various embodiments, the load applying assembly may comprise a pin 610 that is sized to move axially within a cavity 323 formed in the handle case 321. A measurement spring 612 is located within the cavity 323 for biasing the pin 610 in a distal direction "DD". As will be further discussed below, the measurement spring 612 may be sized to apply an 8 gram or other predetermined load to close the jaws 314, 316 when the closure trigger 326 has been pivoted to a certain position. The distal end of the pin 614 may be pivotally coupled to the scale arm 560 by a pin 620 that is received in an elongated slot 563 formed in the bottom end of the scale arm. See FIGS. 10-12. A reference scale 566 may be attached to or formed on the upper end of the scale arm 560 as shown. The reference scale 566 may be provided with reference indicia 568, the purpose of which will be discussed in further detail below. Also in the embodiment depicted in FIG. 8, a shroud 630 may protrude from the bell crank 530. The shroud 630 may have a first reference window 632 therethrough. In addition, a window 329 is also provided through the handle case 321 to enable the surgeon to read the reference indicia 568 on the reference scale 566 that is aligned therewith. See FIG. 10.

Figure 10:
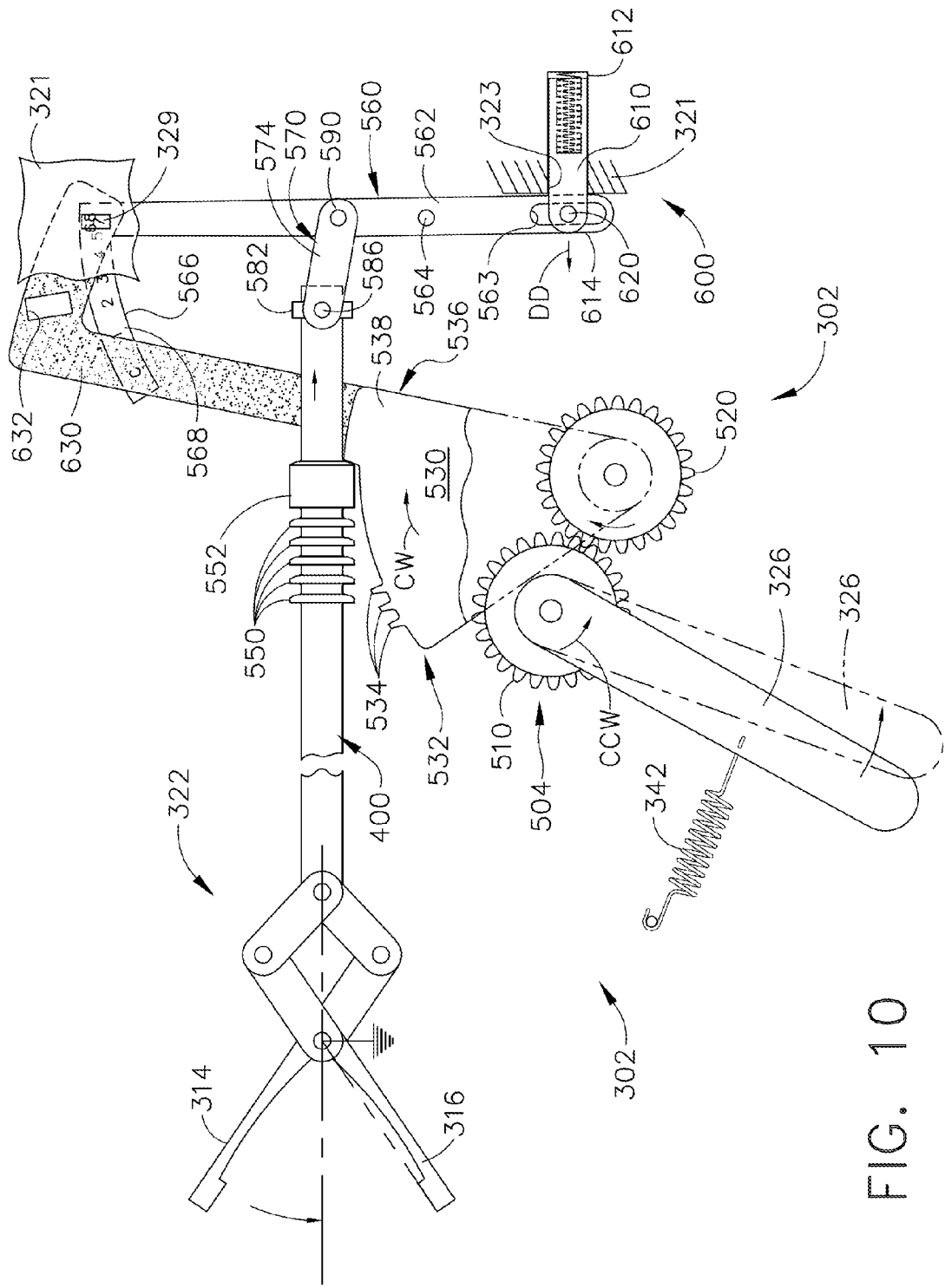
FIG. 10 is a schematic view of various components of the grasper embodiment of FIG. 8 with the jaws thereof in an open position.
Figure 11:
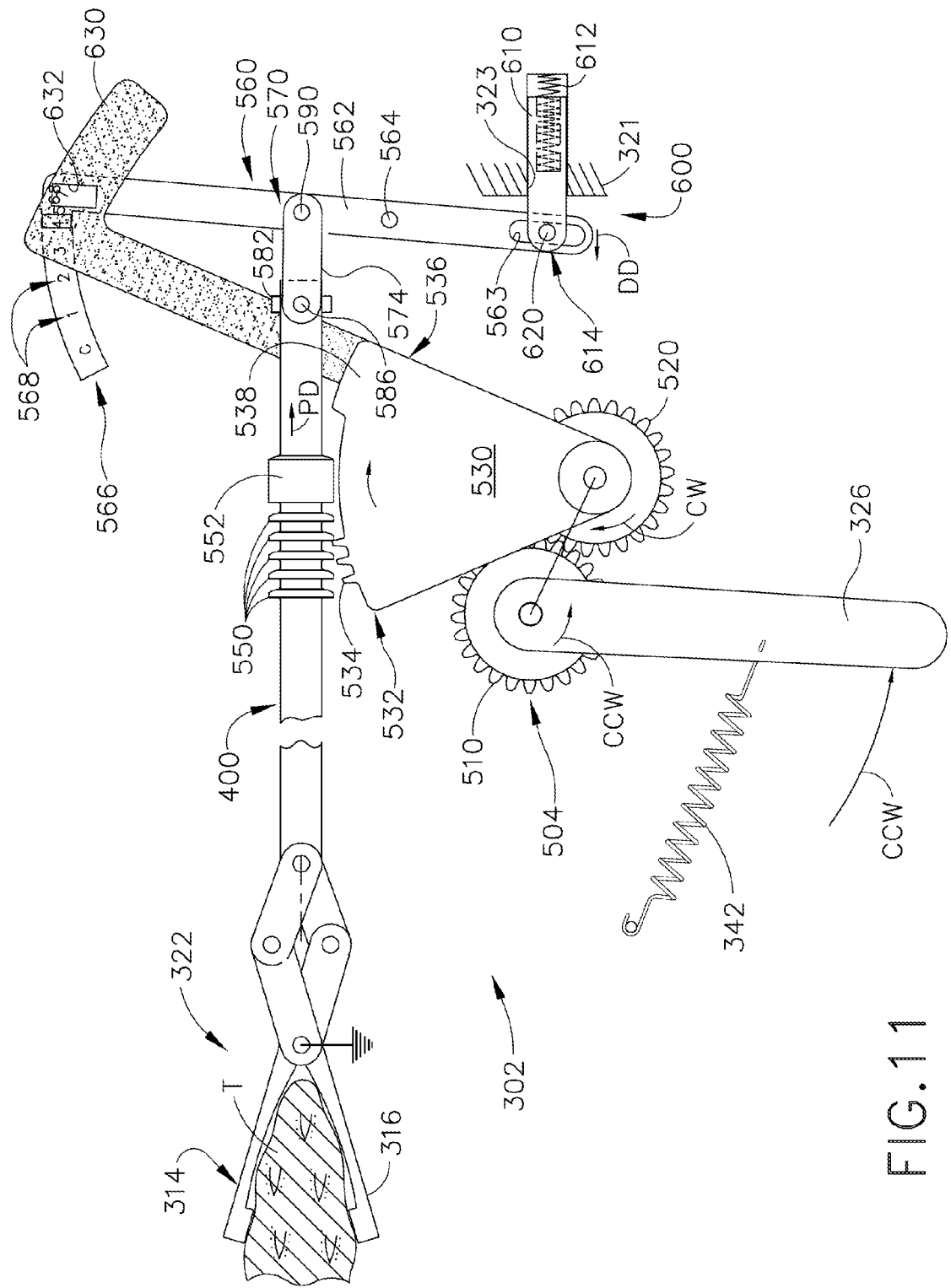
FIG. 11 is another schematic view of various components of the grasper embodiment of FIG. 8 with the jaws thereof clamping a portion of tissue therebetween.
Figure 12:
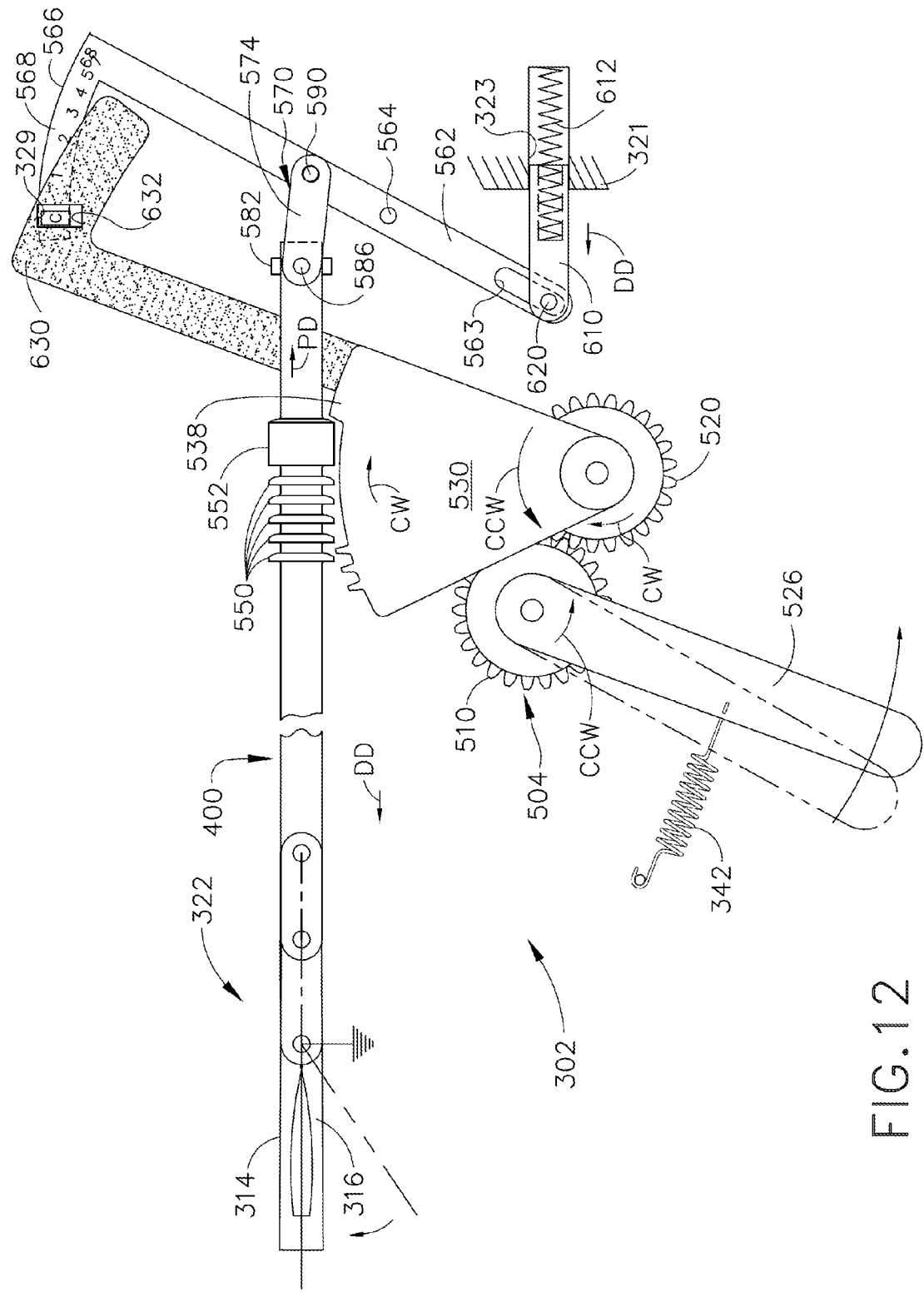
FIG. 12 is another schematic view of various components of the grasper embodiment of FIG. 8 with the jaws thereof in a fully closed position.

The operation of the grasper 302 may be further appreciated from reference to FIGS. 10-12 which schematically illustrate one method of operation. FIG. 10 illustrates the grasper 302 in schematic form with the jaws 314, 316 in the fully open position. When in that position, the closure spring 342 biases the closure trigger 326 away from the grip portion (not illustrated in FIG. 10). The closure spring 342 may be sized relative to the measurement spring 612 such that the closure spring 342 is stronger than the measurement spring 612 to cause the closure trigger 326 to be pivoted to the open position when the grasper 302 is unactuated. In FIG. 10, the closure spring 342 is biasing the closure trigger 326 in the counterclockwise "CCW" direction. As can be seen in FIGS. 8 and 10, when the grasper rod 400 is in the fully opened position, none of the teeth 534 on the bell crank 530 are in engagement with any of the rings 550 on the grasper rod 400 and the retention tab 538 on the bell crank 530 is in contact with the lug 552 on the grasper rod 400. In addition, the end of the shroud 630 extends between the reference scale 566 and the viewing window 329 in the handle case 321 so that the surgeon will only see the shroud 630 when looking through the window 329; no reference indicia 568 would be viewable in the window 329.

FIG. 11 illustrates use of the grasper 302 in schematic form to measure the thickness "t" of the tissue "T". As can be seen in that Figure, the closure trigger 326 has been pulled in the CCW direction against the closing force of the closing spring 342 to cause the bell crank 530 to rotate in the CW direction to move the retention tab 538 out of engagement with the lug 552 on the grasper rod 400. When the retention tab 538 has been moved out of engagement with lug 552, the grasper rod 400 is caused to move in the proximal direction "PD" by means of scale arm 560. In particular, the lower end 562 of the scale arm 560 is moved in the distal direction by the pin 610 which causes the scale arm 560 to pivot about the pivot pin 564 and pull the grasper rod 400 in the proximal direction "PD". As the measurement spring 612 expands, the position where the pin 610 engages the scale arm 560 in the slot 563 will change—moving further from the pivot rod 564. Thus, as the measurement spring force reduces (resulting from extension of the measurement spring 612), the mechanical advantage of the scale arm 560 would increase to maintain a constant load on the grasper jaws 314, 316. As the grasper rod 400 moves in the proximal direction "PD", it causes the jaws 314 and 316 to close upon the tissue "T". In various embodiments, the measurement spring 612 may be sized such that a predetermined amount of clamping load is applied to the tissue "T". For example, in one exemplary embodiment, the measurement spring 612 is sized such that approximately eight grams of closure load is applied to the tissue "T".

When in the tissue "T" has been clamped between the jaws 314, 316 solely under the clamping load of the measurement spring 612, a corresponding one of the reference indicia 568 will be aligned with the viewing window 329 in the handle case 321. The surgeon can then position the closure trigger 326 to cause the bell crank 530 and shroud 630 to move to a position wherein the viewing window 632 in the shroud 630 is in alignment with the viewing 329 window to permit the surgeon to view the reference indicia 568 through the viewing windows 329, 632 as shown in FIG. 11. When in that position, the bell crank 530 is not influencing the position of the grasping rod 530. The position of the grasping rod 400 is solely controlled by the influence of the measuring spring 612 on the scale arm 560 in the manner described above. Thus, when in that position, the surgeon is viewing the reference indicia 568 associated with the thickness of the tissue "T" as it is clamped between the jaws 314, 316 under that predetermined load. Those of ordinary skill in the art will appreciate that the measurement spring and measurement lever may be constructed/calibrated such that the reference indicia 568 correspond to the thickness of the tissue "T" that is clamped under that load.

FIG. 12 illustrates the position of the various grasper components when the surgeon has completely closed the jaws 314, 316 with no tissue clamped therebetween. As can be seen in that Figure, the surgeon has pulled the closure trigger 326 to the point wherein the measurement spring 612 has biased the scale arm 560 to pull the grasper rod 400 far enough in the proximal direction "PD" to cause the jaws 314, 316 to completely close. When the surgeon releases the closure trigger 326, the closure spring 342, which is stronger that the measurement spring 612, biases the closure trigger 326 to the open position. As the closure trigger 326 rotates to the open position, it causes the bell crank 530 to pivot in the CCW direction in FIG. 12 to bring the retainer tab 538 into engagement with the lug 552 on the grasper rod 400 to drive the grasper rod 400 in the distal direction "DD" until the grasper rod 400 reaches the open position (FIG. 10).

Thus, various embodiments of the grasper 302 may be used in the following manner. The surgeon may initially close the jaws 314, 316 to enable the implement portion 322 to be inserted through the cannula or other opening. After the implement portion 322 has been inserted into the patient, the surgeon may release the closure trigger 326 to permit the jaws 314, 316 to open. The surgeon may then manipulate the instrument until the target tissue "T" is oriented between the jaws 314, 316. The jaws 314, 316 may then be closed on the target tissue "T" by depressing the closure trigger 326 towards the grip portion 336 of the handle assembly 320. As the surgeon continues to depress the closure trigger 326, he or she can observe the viewing window 329 in the handle assembly 320 until the reference indicia 568 which corresponds to the tissue thickness under a predetermined clamping load is viewable. Further depressing of the closure trigger 326 would further draw the grasper rod 400 in the proximal direction "PD" by virtue of the engagement of the teeth 534 on the bell crank 530 with one or more rings 550 on the grasper rod 400 and thereby apply further clamping force to the tissue "T". In doing so, however, the movement of the bell crank 530 and shroud 630 causes the viewing window 632 in the shroud 630 to move out of alignment with the viewing window 329 in the handle casing 321. Thus, the surgeon is unable to view the reference indicia 568 when the tissue "T" has been placed under a clamping load that is greater than the desired predetermined clamping load. If the surgeon desires to take a thickness reading, he or she simply must start to release the closure trigger 326 until the window 632 in the shroud 630 once again aligns with the window 329 in the handle casing to permit viewing of the reference indicia.

Figure 13:
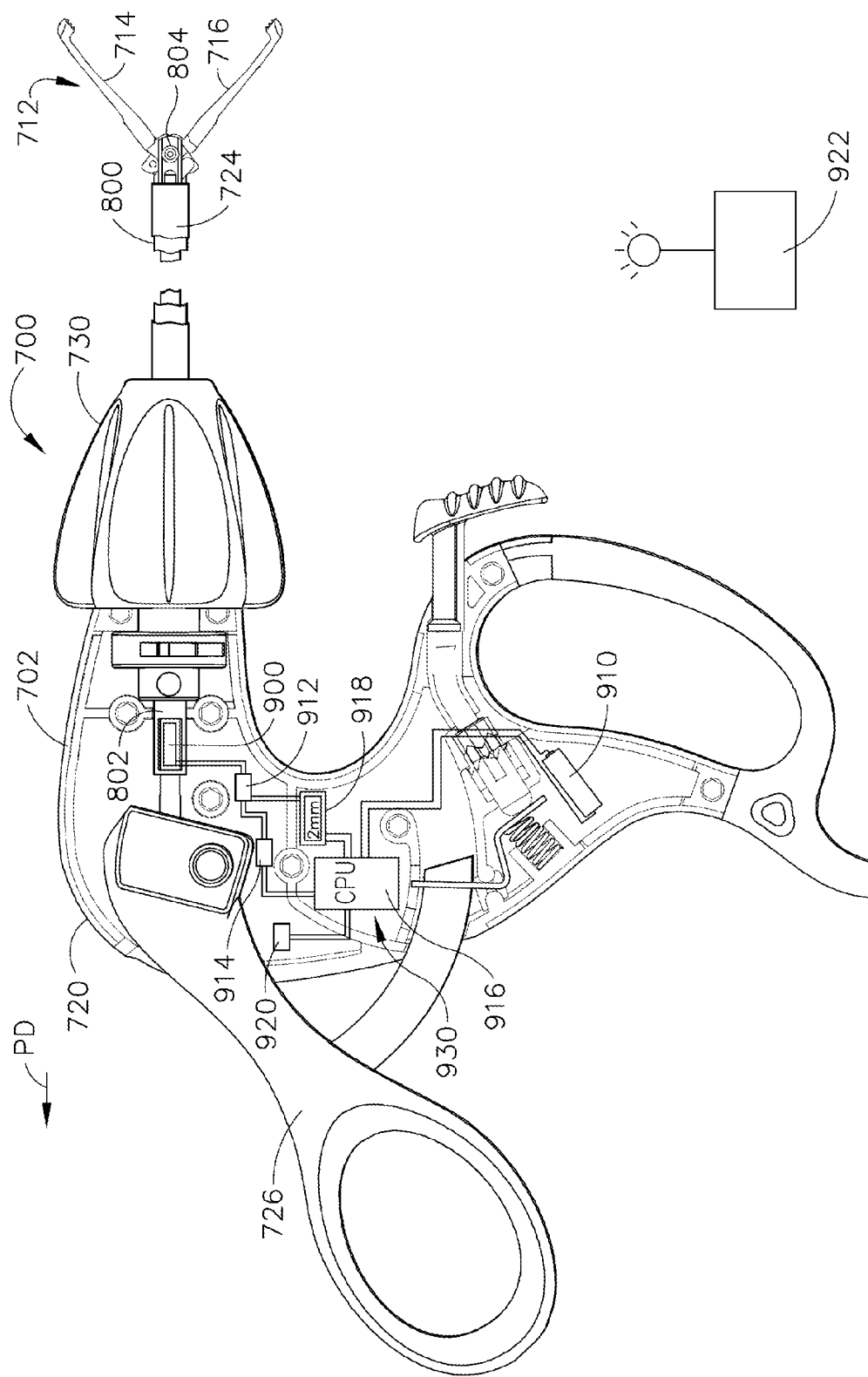
FIG. 13 is a right side elevational view of another grasper embodiment of the present invention.

FIG. 13 illustrates another surgical instrument 700 in the form of a grasper 702 that may employ various unique and novel features of various embodiments of the present invention. In this embodiment, a conventional grasper arrangement may be employed. Such grasper 702 may include an end effector 712 that has a first jaw 714 and a second jaw 716 that are operably mounted to a grasper rod 800 that protrudes distally from a handle assembly 720. As is known, a proximal portion 802 of the grasper rod 800 is rotatably supported within the handle assembly 720 and coupled to a rotation knob 730 rotatably supported on the handle assembly 720. Such arrangement permits the surgeon to rotate the grasper rod 800 relative to the handle assembly 720. As can also be seen in FIG. 13, the grasper rod 800 may extend through a closure tube 724 that also protrudes from the handle assembly 720.

As is known in the art, the jaws 714 and 716 may be pivotally coupled to a distal end 804 of the grasper rod 800 and may be retained in the open position illustrated in FIG. 13 by a spring arrangement (not shown). The jaws 714 and 716 are caused to close when their proximal ends 715, 717, respectively are brought into contact with a distal end 725 of the closure tube 724 as the grasper rod 800 is drawn in the proximal direction in response to the actuation of a closure trigger 726 attached to the handle assembly 720. The construction and operation of the closure trigger and its interaction with the grasper rod 800 are known in the art and therefore will not be discussed in detail herein.

Figure 14:
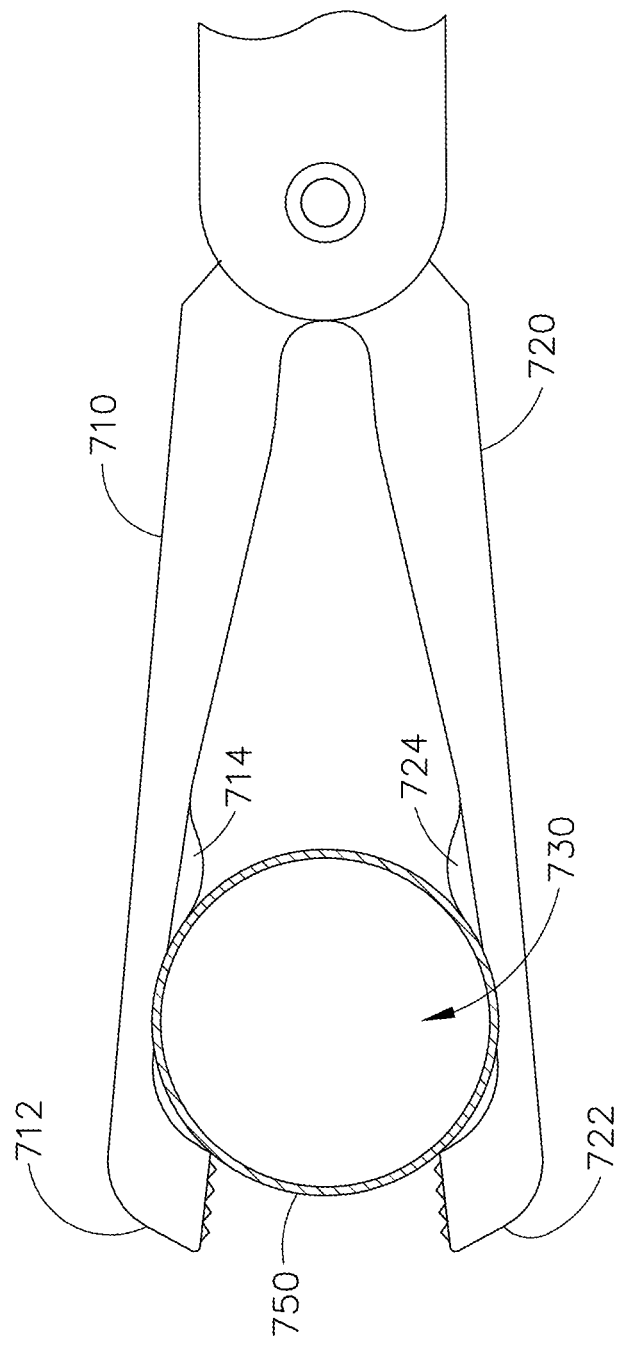
FIG. 14 is a side elevational view of a jaw arrangement of other embodiments of the present invention.

In various embodiments, however, a strain gauge 900 may be oriented for interaction with the grasper rod 800 such that as the grasper rod is moved in the proximal direction "PD" by depressing the closure trigger 726, the strain gauge 900 measures the strain on the closure rod 800. As can be seen in FIG. 14, the strain gauge 900 is coupled to a battery or other source of electrical power 910, an amplifier 912, a digital-to-analog converter 914, a conventional central processing unit "CPU" 916, and a display unit 918. In various embodiments, the strain gauge 900, source of electrical power 910, the amplifier 912, converter 914 and CPU 916 may be collectively referred to as an output generator, generally designated as 930. In alternative embodiments, the CPU 916 may also be coupled to a wireless signal generator 920 that transmits the thickness data to a remote monitor 922.

In this embodiment, the CPU 916 employs an algorithm that compares the strain values over time and waits until the strain is no longer changing within a given delta for example, less than 1 to 2% variation, before it displays the final load reading or calculated tissue thickness "t" on the display. Such variation may be measured in raw voltage (strain gauge acts as a resistor to modify voltage according to how much it is stressed or pulled or compressed), deflection after the data is translated from voltage to strain, or tissue thickness when the strain is translated into thickness. In addition, a switch (mechanically or electrically activated) could be associated with the clamping trigger for detecting the position of the clamping trigger. The switch 164 may communicate with the CPU 156 such that the CPU 156 would not start to process the strain loads until the closure trigger 26 reached a predetermined position.

Figure 15:
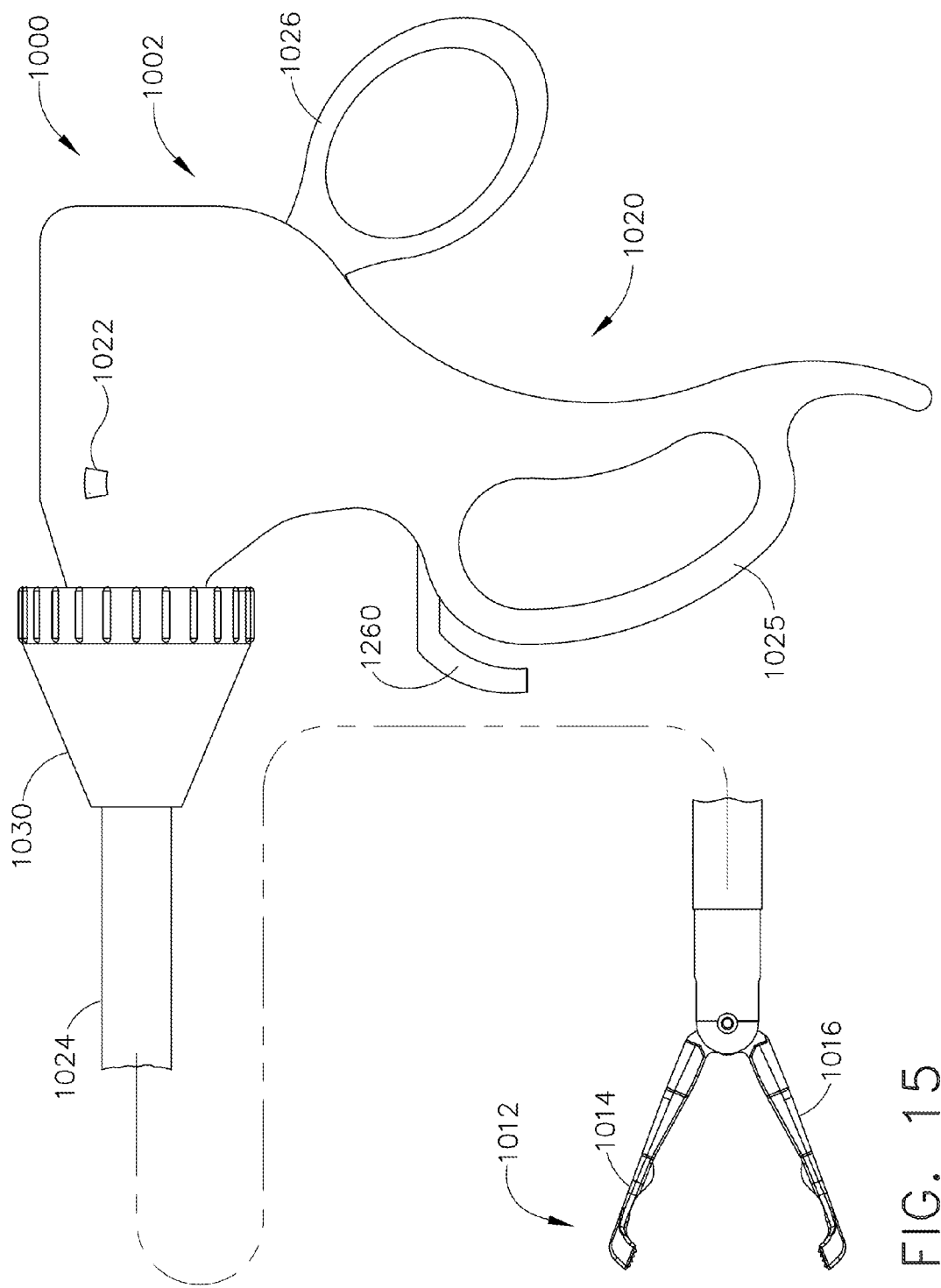
FIG. 15 is a side view of another surgical instrument embodiment of the present invention.

Another feature of various embodiments of the present invention is depicted in FIG. 14. In particular, FIG. 14 illustrates jaws 710, 720 that may be used in connection with any of the grasper embodiments described herein or other conventional grasper arrangements wherein it may be advantageous to grasp and manipulate another surgical instrument such as, an endocutter or the like. In the embodiment depicted in FIG. 15, the first jaw 710 may have a clamping face 711 and a distal end 712 that curves downward. The second jaw 720 has a clamping face 721 and a distal end 722 that curves upwardly. A somewhat curved nodule 714 may be formed on the clamping face 711 of the first jaw 710 and another somewhat curved nodule 724 may be formed on the clamping face 721 of the second jaw 720. In this embodiment, the nodules 714, 724 may be so oriented and shaped to cooperate with the respective distal ends 712, 722 of the first and second jaws 710, 720 so as to form a cradle, generally designated as 730, for receiving and supporting a portion of a surgical instrument 750 that has a substantially circular cross-sectional shape. Such arrangement serves to provide a positive support for the surgical instrument 750 within the first and second jaws 710, 720 and enables the surgeon to accurately manipulate the instrument 750 using the grasper. Those of ordinary skill in the art will understand that, in other embodiments of the present invention, the sizes, shapes and numbers of nodules may vary and/or the distal ends of the jaws may have different shapes to better form a cradle that corresponds to the cross-sectional shape of the instrument to be grasped between the jaws. Thus, the scope and protection afforded to these various embodiments should not be limited to use of two nodules having the specific shapes illustrated in FIG. 14.

Figure 18:
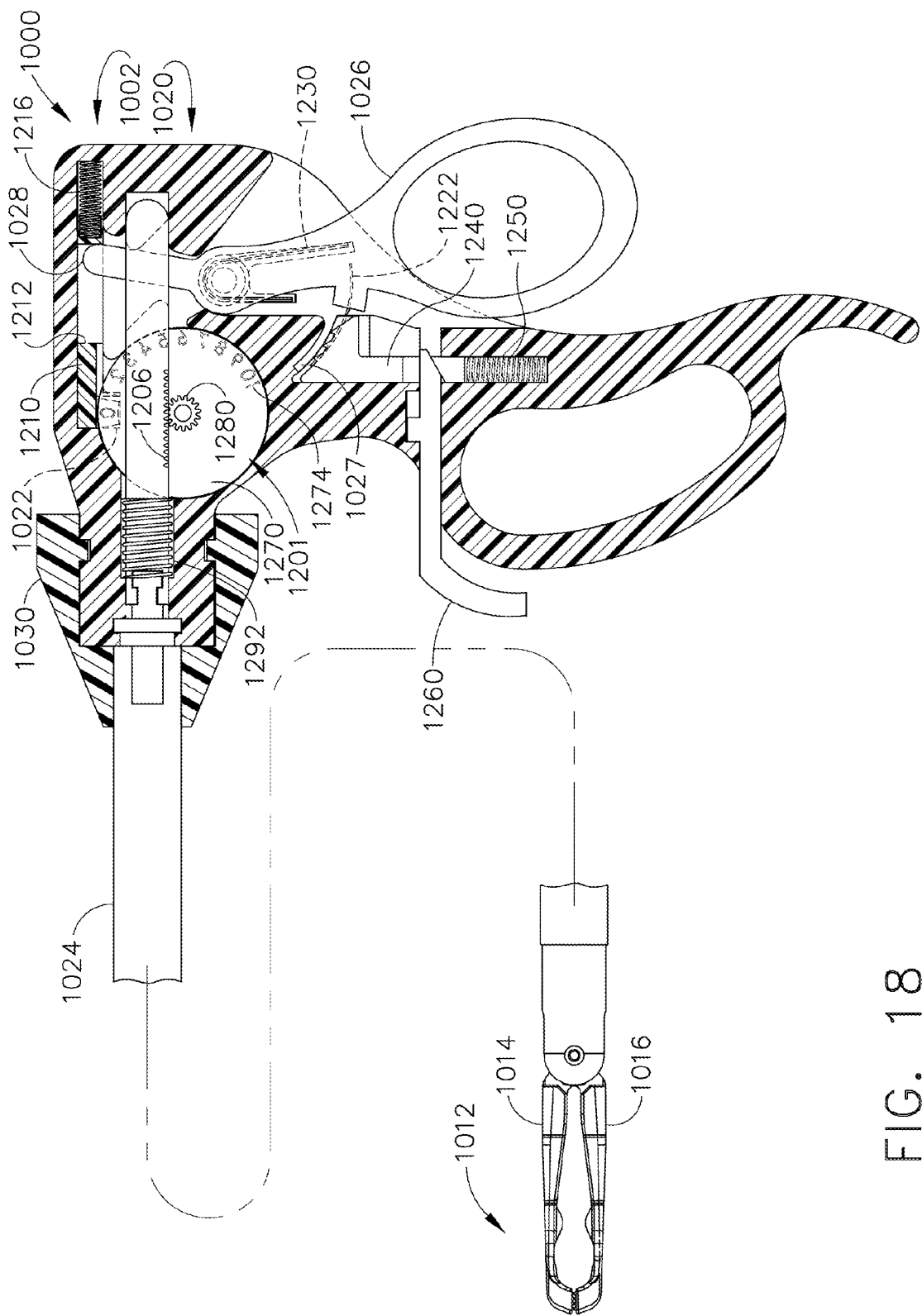
FIG. 18 is a cross-sectional view of the surgical instrument of FIGS. 15-17 in a fully closed and locked position with some components thereof shown in solid form for clarity.
Figure 19:
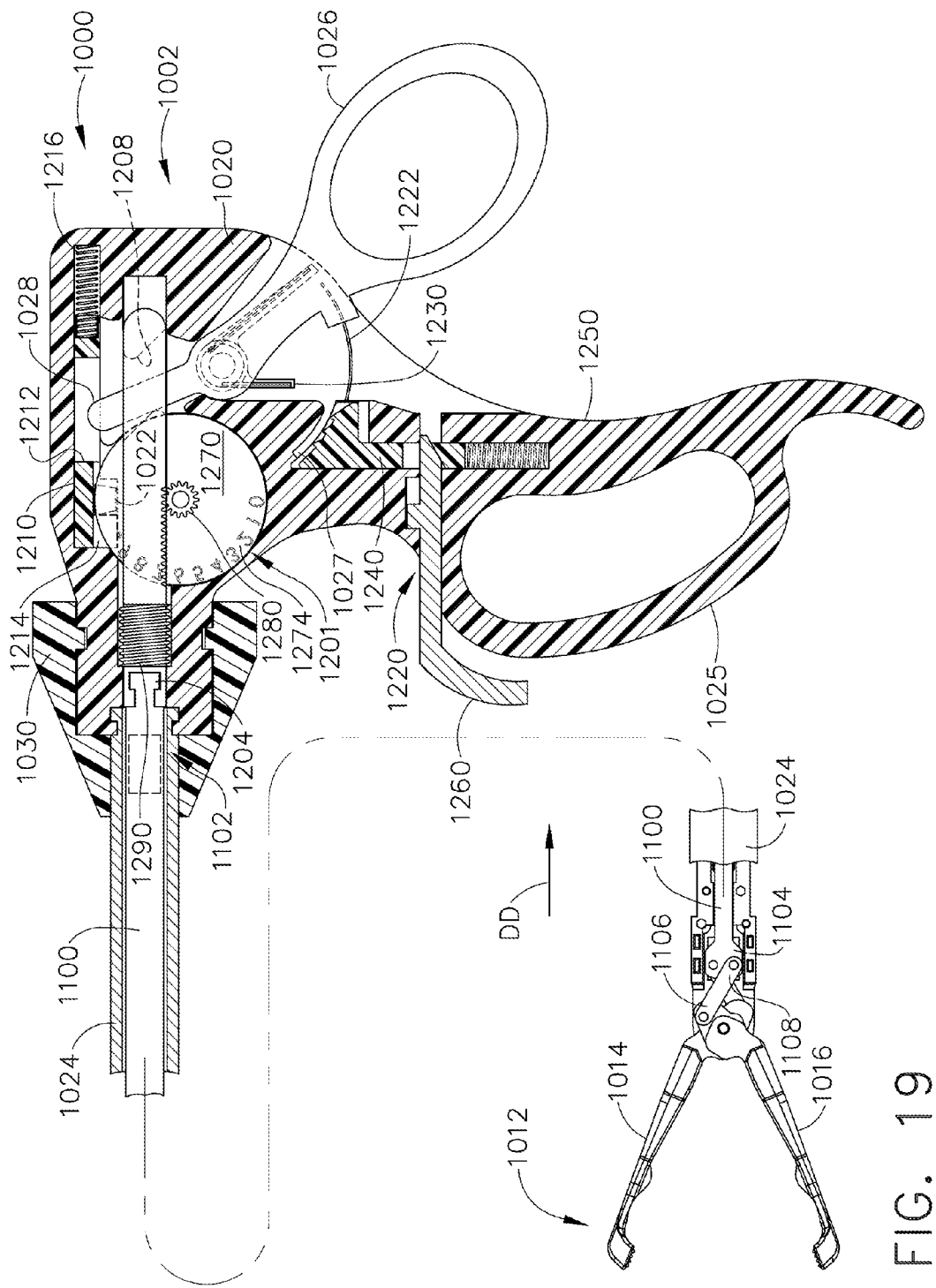
FIG. 19 is another cross-sectional view of the surgical instrument of FIGS. 15-18 in a fully open position with some components thereof shown in solid form for clarity.
Figure 20:
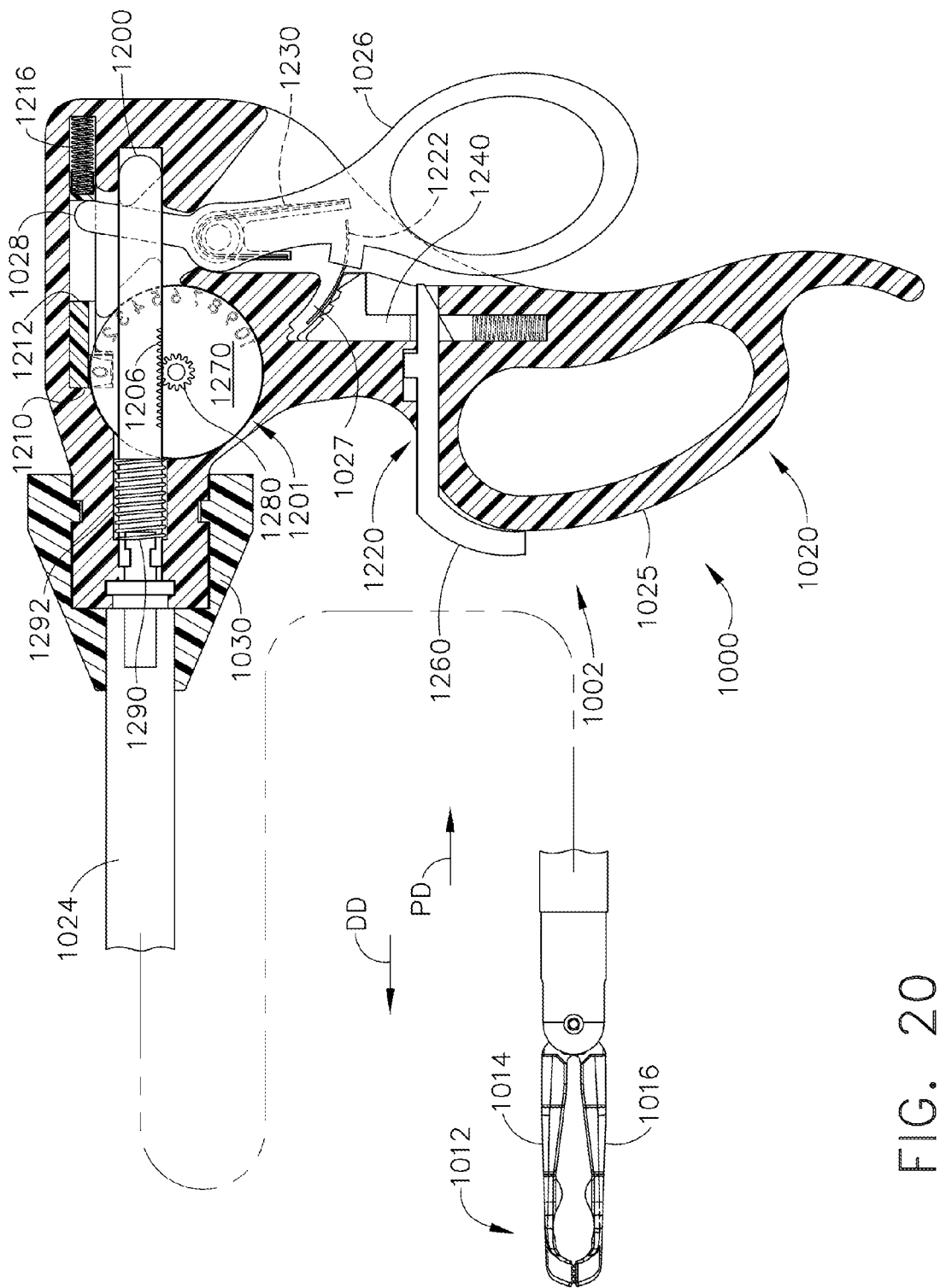
FIG. 20 is another cross-sectional view of the surgical instrument of FIGS. 15-19 in a fully closed position and with the release trigger in a fully depressed position with some components thereof shown in solid form for clarity.

FIGS. 15-23 illustrate another surgical instrument 1000 in the form of a grasper 1002 that may employ certain unique and novel features of various embodiments of the present invention. In various embodiments, the grasper 1002 may include an end effector 1012 that has a first jaw 1014 and a second jaw 1016 that are operably mounted to a grasper rod 1100 that protrudes distally from a handle assembly 1020. See FIG. 19. The grasper rod 1100 may be axially received within a tube 1024 that may be rotatably affixed to the handle assembly 1020. A rotation knob 1030 may be rotatably affixed to the handle assembly 1020 as shown in FIG. 19 and be attached to the tube 1024 such that rotation of the rotation knob 1030 relative to the handle assembly 1020 may also result in the rotation of the end effector 1012 relative to the handle assembly 1020. The jaws 1014 and 1016 may be pivotally coupled to a distal end 1104 of the grasper rod 1100 by corresponding linkages 1106, 1108. Movement of the grasper rod 1100 in the distal direction "DD" will cause the jaws to 1014, 1016 to pivot closed.

In various embodiments, the grasper rod 1100 may be selectively moved by actuation of a closure trigger 1026 that is pivotally supported by the handle assembly 1020. More specifically and with reference to FIGS. 17 and 18, a proximal end 1102 of the grasper rod 1100 may be attached to a calibrated spring slide 1200 housed within the handle assembly 1020. In various embodiments for example, the proximal end 1102 of the grasper rod 1100 may be formed with a T-shaped portion 1103 that is configured to be received in a correspondingly shaped cavity 1204 in a distal end portion 1202 of the calibrated spring slide 1200. The calibrated spring slide 1200 is configured to be movably received in an elongated opening 1040 in the handle assembly 1020 and has an actuator opening 1208 therein for receiving a lever arm 1028 formed on the closure trigger 1026. The lever arm 1028 may also protrude through the actuator opening 1208 into a corresponding opening 1212 in a window slide 1210 that is configured to be slidably supported within a window slide cavity 1040 formed in the handle assembly 1020. The widow slide 1210 may have blocking portions 1214 formed thereon that, as will be discussed in further detail below, serve to block corresponding window openings 1022 formed in the handle assembly 1020. Thus, by pivoting the closure trigger 1026 toward the pistol grip portion 1025 of the handle assembly 1020, the lever arm 1028 causes the calibration spring slide 1200 and the window slide 1210 to move in the proximal "PD" direction. In various embodiments, a window slide spring 1216 may be supported by the handle assembly 1020 to bias the window slide 1210 in the distal "DD" direction.

As can also be seen in FIGS. 16-23, the grasper 1002 may also be configured with a releasable lock assembly, generally designated as 1220. In various embodiments, the lock assembly 1220 may comprise a lever lock arm 1222 that is attached to or protrudes from the closure trigger 1026 that is pivotally journaled on a pivot stud 1023 or other member formed on or otherwise attached to the handle assembly 1020. See FIG. 16. A torque spring 1230 may also be journaled on the pivot stud 1023 to apply a biasing force to the closure trigger 1026 to bias the closure trigger 1026 to an open position as illustrated in FIG. 18. In various embodiments, the lever lock arm 1222 may comprise a piece of metal or other suitable material that is attached to the closure trigger 1026 and is configured to extend into a lock cavity 1027 formed in the handle assembly 1020. Extending into the lock cavity 1027 is a lock member that has a serrated or toothed end 1242 that is configured to selectively engage a portion of the lever lock arm 1222 and retain it within the lock cavity 1027. As shown in FIGS. 16-23, a lock spring 1250 may be supported in the handle assembly 1020 for biasing the lock member 1240 into retaining engagement with a portion of the lever lock arm 1222. To enable the clinician to selectively release the lock member 1240 out of retaining engagement with the lever lock arm 1222, a release trigger 1260 may be provided. In various embodiments, the release trigger 1260 may have a proximal end 1262 portion that is slidably received within a trigger cavity 1029 in the handle assembly. The proximal end 1262 of the release trigger 1260 is also configured to extend into a cavity 1244 formed in the lock member 1240. Depressing the release trigger 1260 toward the pistol grip portion 1025 of the handle assembly 1020 causes the proximal end 1262 of the release trigger 1260 to cooperate with an angled surface 1246 within the cavity 1244 to cause the lock member 1240 to moved downwardly against the lock spring 1250 to enable the lever lock arm 1222 to be released from the lock cavity 1027. When the lever lock arm 1222 is released, the closure trigger 1026 may pivot to an open position under the influence of the torque spring 1230.

Figure 16:
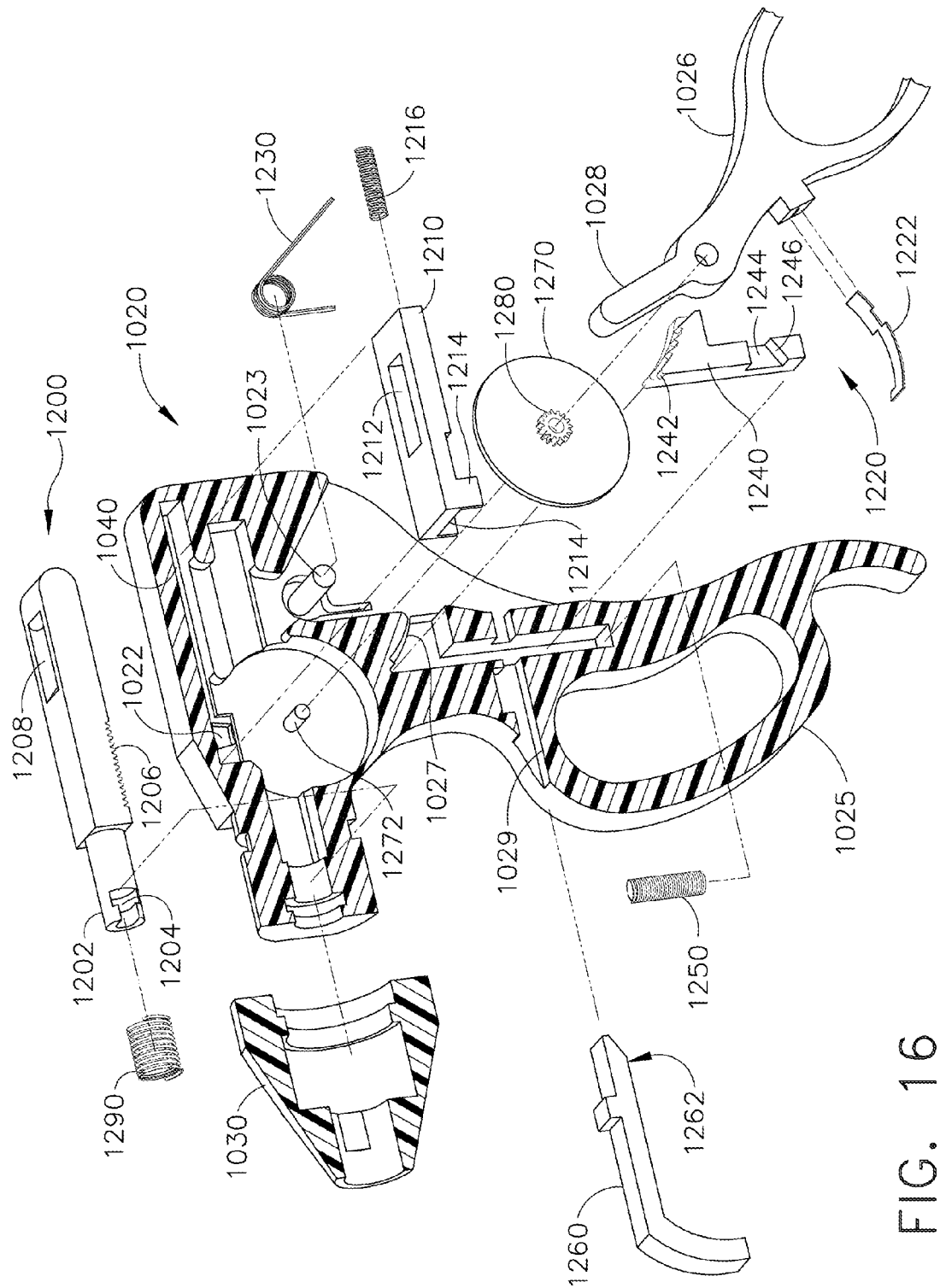
FIG. 16 is an exploded assembly view of a portion of the surgical instrument of FIG. 15.
Figure 17:
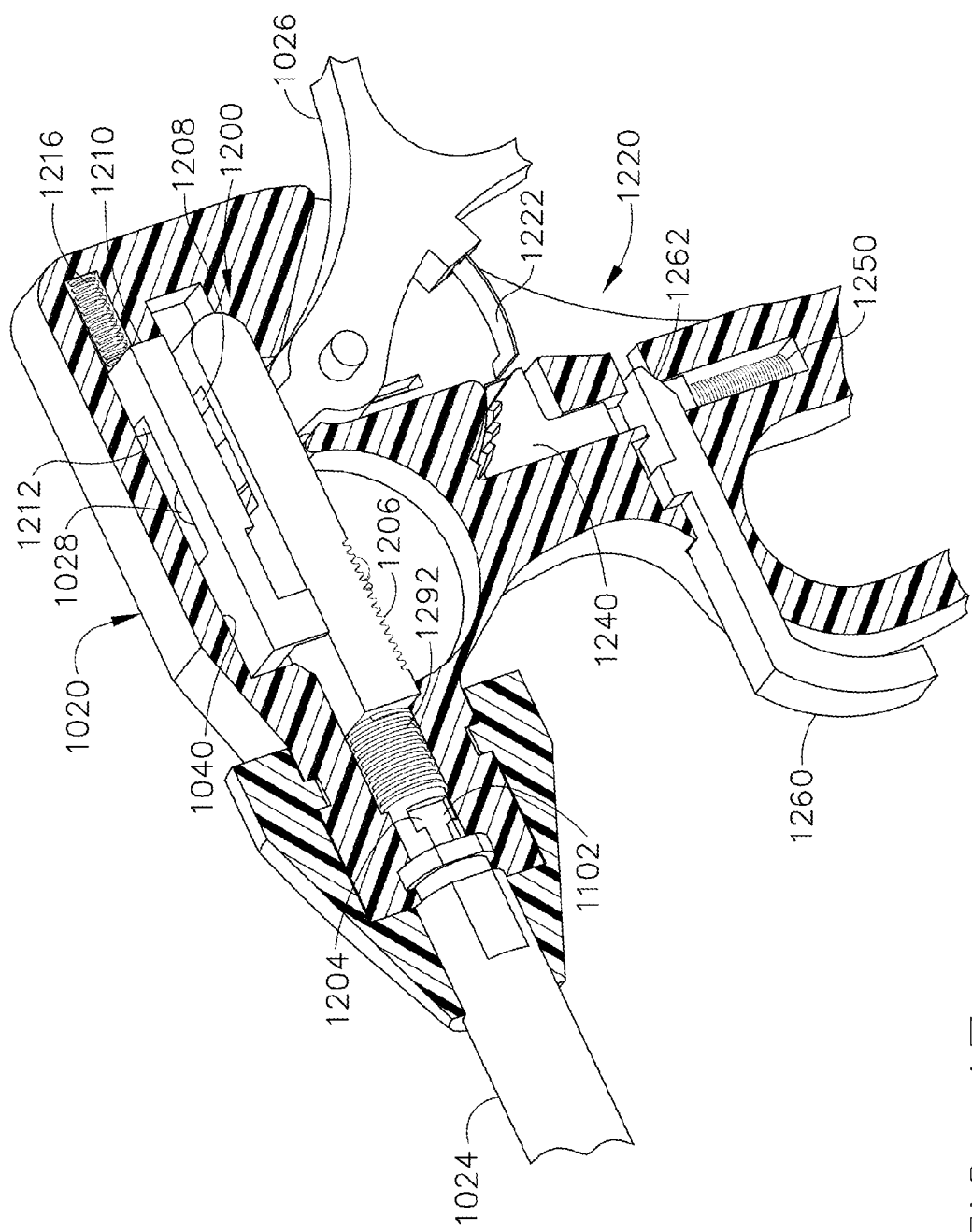
FIG. 17 is a cross-sectional view of a handle assembly of the surgical instrument of FIGS. 15 and 16 with some components thereof shown in solid form for clarity.

Various embodiments may further include an output generator generally designated as 1201. In various embodiments, the output generator may include a reference dial 1270 that is rotatably supported on a dial stud 1272 formed or otherwise supported within the handle assembly 1020. The reference dial 1270 may be provided with reference indicia 1274, the purpose of which will be discussed in further detail below. In addition, the output generator 1201 may further include drive gear 1280 may be formed or otherwise attached to the reference dial 1270 as shown in FIG. 16. The drive gear 1280 is arranged for meshing engagement with gear teeth 1206 formed on the calibrated spring slide 1204. Also in various embodiments, the output generator may, for example, include a calibrated spring 1290 provided on the distal end 1202 of the calibrated spring slide 1200 and be received within a corresponding cavity 1292 in the handle housing 1020. As will be appreciated from the discussion to follow, the output generator 1201 in various embodiments is mechanically actuated or powered. As used herein, the term "mechanically actuated" means that the output generator is actuated without any electrically generated input.

Figure 23:
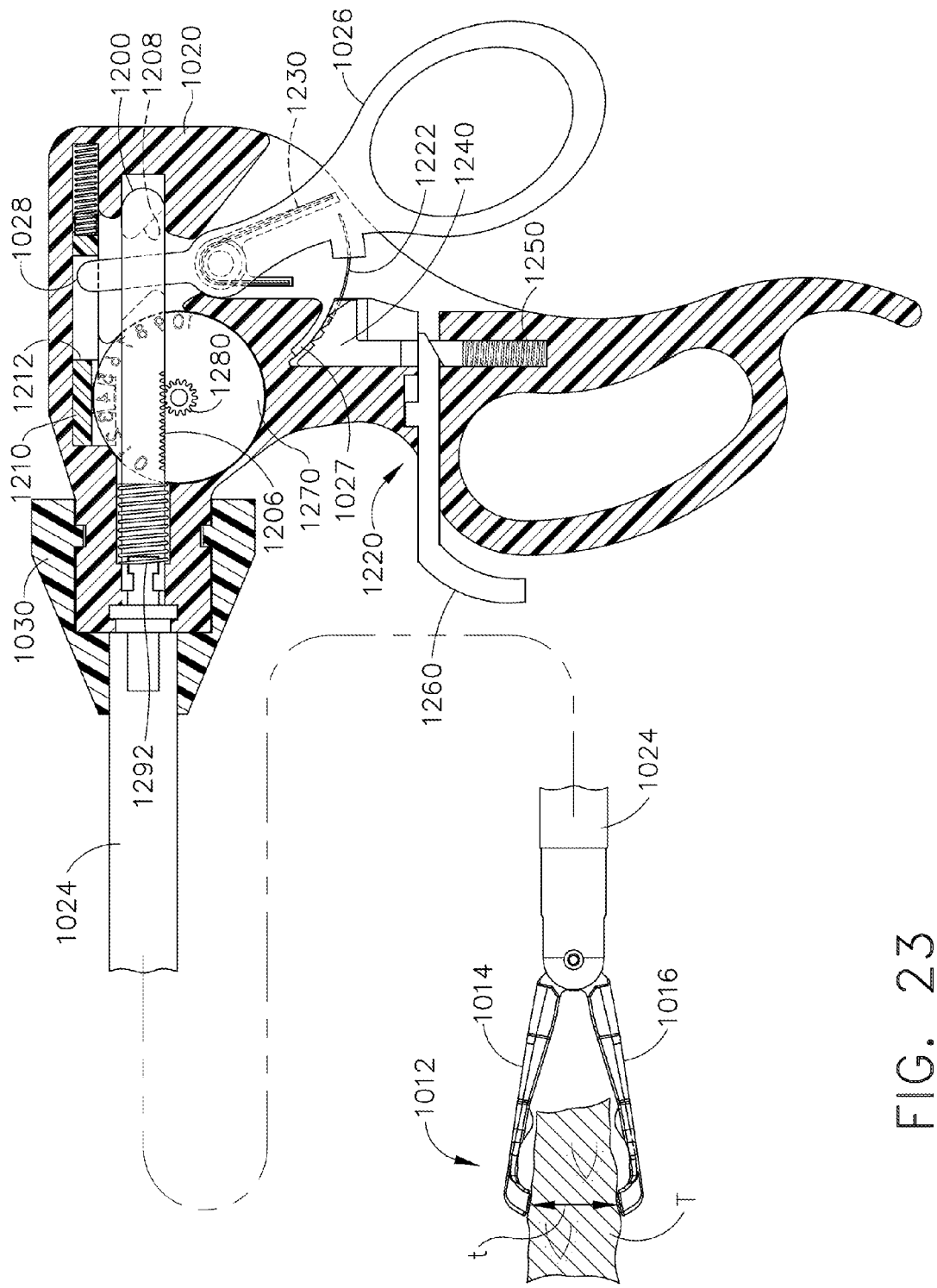
FIG. 23 is another cross-sectional view of the surgical instrument of FIGS. 15-22 in a tissue clamping position wherein the user can read the reference indicia corresponding to a thickness "t" of the tissue clamped thereby.

Operation of various embodiments of the grasper 1002 may be understood from reference to FIGS. 18-23. FIG. 18 illustrates the grasper 1002 in a "fully closed" and locked position. When the closure trigger 1026 is in the fully depressed position, the lever arm 1028 is positioned within the lever arm cavity 1208 in the calibrated spring slide 1200 to permit the calibrated spring slide 1200 to slide proximally under the biasing force created by the calibration spring 1292. As the calibrated spring slide 1200 moves proximally, it drives the reference dial 1270 in a clockwise direction by virtue of the meshing engagement between the teeth 1206 and the drive gear 1280. In various embodiments, the calibrated spring 1292 may be sized such that the "0" on the reference dial 1270 is aligned with the window 1022 in the handle assembly 1020. To return to a fully open position (FIG. 19), the clinician depresses the release trigger 1260 as shown in FIG. 23 which releases the lever lock arm 1222 and permits the closure trigger 1026 to return to the open position under the force of the torque spring 1230. As the closure trigger 1026 moves to the open position, the lever arm portion 1028 pivots in a counterclockwise direction within the opening 1212 in the window slide 1210 thereby permitting the window slide 1210 to be biased in the distal direction by the window slide spring 1216 such that the blocking portions 1214 block the windows 1022 in the handle assembly 1020. In addition, the lever arm portion 1028 pushes the calibrated spring slide 1200 distally which moves the grasper rod 1100 distally to open the jaws 1014 and 1016.

Figure 21:
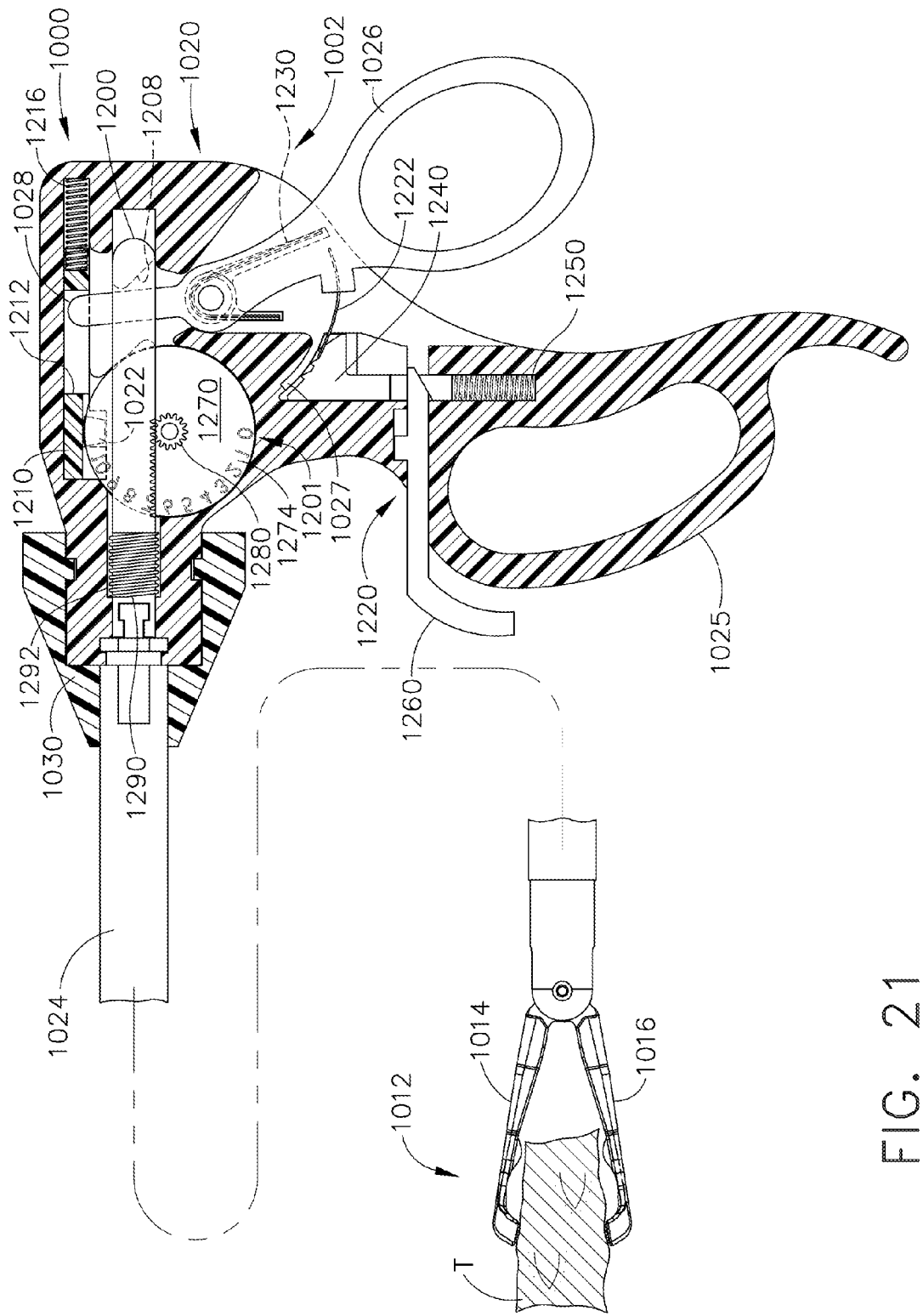
FIG. 21 is another cross-sectional view of the surgical instrument of FIGS. 15-20 in a tissue clamping position with some components thereof shown in solid form for clarity.
Figure 22:
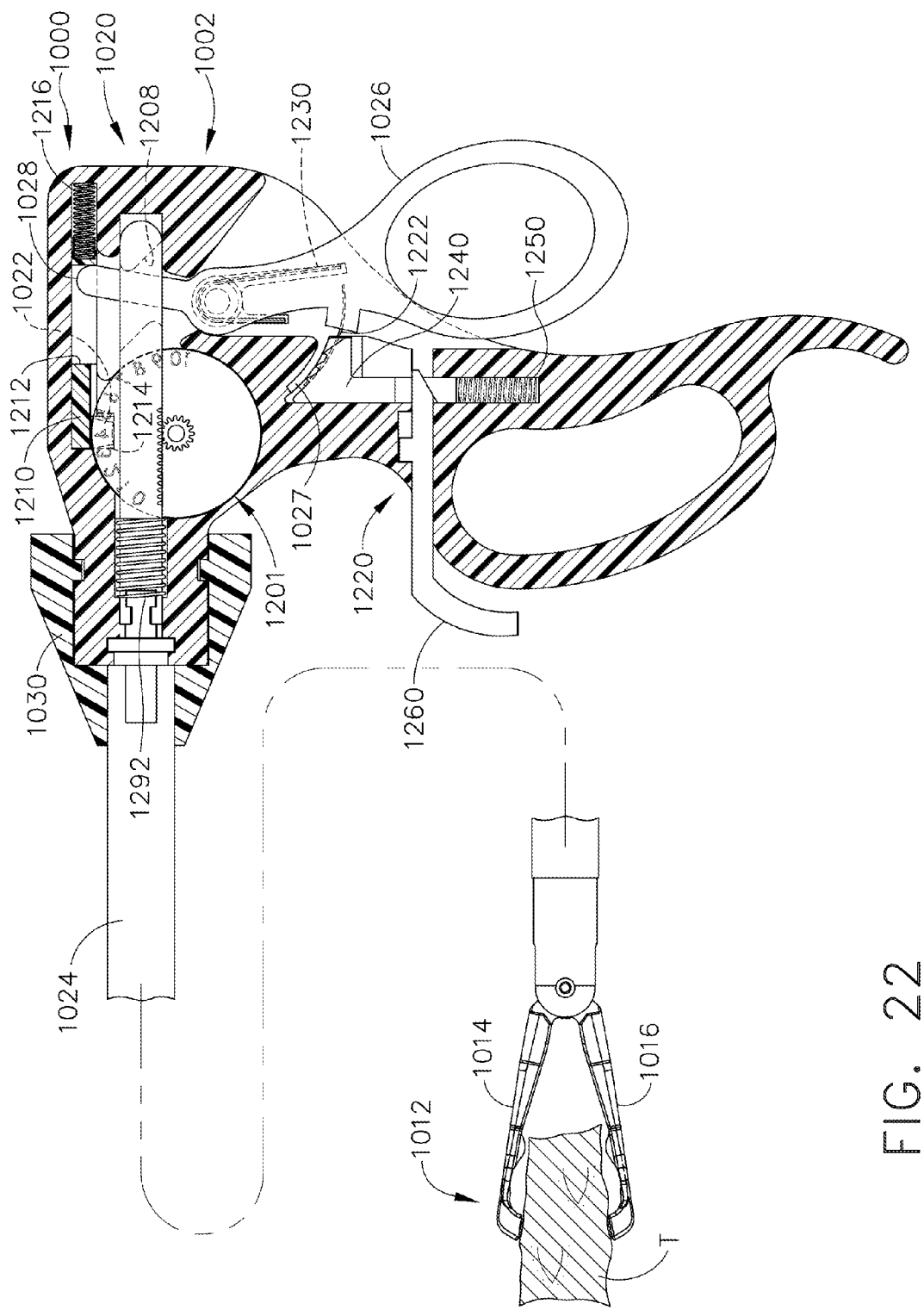
FIG. 22 is a cross-sectional view of the surgical instrument of FIGS. 15-21 in a position wherein the clinician is applying excessive clamping force to the tissue with some components thereof shown in solid form for clarity.

When the clinician desires to clamp the tissue "T" between the jaws 1014, 1016 as shown in FIG. 21, the clinician moves the end effector 1012 into position and depresses the release trigger 1260 to permit the closure trigger 1026 to begin to be depressed. When in that position, the window slide 1210 is positioned in its distal-most position and the blocking portions 1214 thereof do not obscure the windows 1022 in the housing assembly. As the closure trigger 1026 is depressed, the calibrated spring slide 1200 moves proximally which draws the grasper rod 1110 proximally and causes the jaws 1014 and 1016 to clamp the tissue "T" therebetween (FIG. 21). The clinician continues to depress the closure trigger 1026 until the closure trigger has pivoted to a point wherein the lever arm portion 1028 biases the window slide 1210 proximally to a position wherein the blocking portions 1214 block the windows 1022 in the handle assembly 1020. See FIG. 22. The clinician thereafter slightly releases the closure trigger 1026 to a point wherein the reference indicia 1274 on the reference dial 1270 is viewable through the windows 1022 in the handle assembly 1020. See FIG. 23. Those of ordinary skill in the art will appreciate that the reference indicia may be associated with a particular thickness "t" of tissue "T". For example, the number 1 on the reference dial 1270 may represent an approximate tissue thickness of 1 mm; the number 2 may represent an approximate tissue thickness of 2 mm and so on. It will be further understood that such unique and novel arrangement enables the clinician to obtain a thickness measurement of the tissue "T" at a predetermined clamping load (resulting from the calibrated spring 1292). For example, the calibrated spring 1292 may be sized to apply an approximate clamping load of 8 grams/mm squared when the grasper is positioned to indicate the tissue thickness. If the clinician "over clamps" the tissue, the window slide 1210 moves to a position wherein the blocking portions 1214 block the windows 1022 to thereby prevent the clinician from reading the reference indicia 1274.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. Those of ordinary skill in the art will readily appreciate the different advantages provided by these various embodiments. For example, various embodiments of the present invention enable the surgeon to determine the thickness of the desired target tissue to enable the properly sized implementations (staple cartridges, etc.) to be employed. Various embodiments are also constructed to enable the surgeon to take such tissue thickness measurements under a predetermined compressive load.

While several embodiments of the invention have been described, it should be apparent, however, that various modifications, alterations and adaptations to those embodiments may occur to persons skilled in the art with the attainment of some or all of the advantages of the invention. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosed invention as defined by the appended claims.

The devices disclosed herein can be designed to be disposed of after a single use, or they can be designed to be used multiple times. In either case, however, the device can be reconditioned for reuse after at least one use. Reconditioning can include an combination of the steps of disassembly of the device, followed by cleaning or replacement of particular pieces, and subsequent reassembly. In particular, the device can be disassembled, and any number of particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those of ordinary skill in the art will appreciate that the reconditioning of a device can utilize a variety of different techniques for disassembly, cleaning/replacement, and reassembly. Use of such techniques, and the resulting reconditioned device, are all within the scope of the present application.

Preferably, the invention described herein will be processed before surgery. First a new or used instrument is obtained and, if necessary, cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or higher energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. A surgical instrument, comprising:
   a pair of opposing jaws, wherein at least one jaw is selectively movable relative to the other jaw in response to opening and closing motions applied to at least one of said opposing jaws for selectively clamping tissue therebetween;
   an output generator associated with said pair of opposing jaws, said output generator generating tissue thickness data representing thicknesses of the tissue clamped between said pair of opposing jaws when said opposing jaws are in a plurality of positions between opened and closed;
   a probe operably interfacing with said output generator, wherein said probe is configured to operably contact both of the jaws when said pair of opposing jaws are in said plurality of positions such that at said plurality of positions said probe causes said output generator to generate said tissue thickness data; and
   a display for displaying said tissue thickness data thereon.

2. The surgical instrument of claim 1 wherein said output generator comprises:
   at least one strain gauge for generating a strain signal corresponding to the tissue thickness of the tissue clamped between said pair of opposing jaws; and
   a processor communicating with said at least one strain gauge for receiving said strain signal therefrom and generating said tissue thickness data corresponding to said strain signal and communicating said tissue thickness data to said display.

3. The surgical instrument of claim 1 wherein said pair of opposing jaws comprises:
   a first jaw sized to removably support a cartridge therein; and
   a second jaw movably coupled to said first jaw and being selectively movable between open and closed positions relative to said first jaw in response to application of said open and closing motions to at least one of said first and second jaws and wherein said output generator comprises:
   a measurement cartridge removably supportable in said first jaw;
   at least one strain gauge associated with said measurement cartridge for generating a strain signal corresponding to the tissue thickness of tissue clamped between the measurement cartridge and the second jaw; and
   a processor communicating with said at least one strain gauge for receiving said strain signals therefrom and calculating said tissue thickness data corresponding to said tissue thickness and communicating said tissue thickness data to said display.

4. The surgical instrument of claim 3 wherein said strain gauge is supported by said measurement cartridge and said probe has a deflectable portion for contact with said second jaw.

5. A surgical instrument comprising:
   a handle assembly;
   an end effector for performing a surgical operation, said end effector coupled to said handle assembly and having opposed jaw members for selectively clamping tissue therebetween in response to opening and closing motions applied to at least one of said opposing jaw members;
   a first signal generator in said end effector for generating first signals corresponding to a thickness of the tissue clamped between said opposed jaw members;
   a nodule oriented on said end effector such that said nodule is aligned with the first signal generator;
   a probe configured to operably contact both of the jaw members when said pair of opposed jaw members are in a plurality of positions between opened and closed such that at said plurality of positions said probe causes a second signal generator operably interfacing with said probe to generate second tissue thickness signals;
   a signal processor for receiving said first and second signals from said first signal generator and said second signal generator and calculating the thickness of the tissue clamped between said opposed jaw members; and
   a display communicating with said signal processor for displaying the tissue thickness thereon.

6. The surgical instrument of claim 5 further comprising a measurement cartridge, comprising a cartridge body sized to be removably supported in said end effector and wherein said first signal generator comprises a first strain gauge supported by said cartridge body and configured to communicate with said signal processor when said cartridge body is removably supported in said end effector, said first strain gauge generating first strain signals corresponding to an amount of compressive load applied to the tissue clamped by said end effector.

7. The surgical instrument of claim 6 wherein said second signal generator comprises a second strain gauge supported within said cartridge body and communicating with said signal processor, said second strain gauge generating at least one second strain signal corresponding to a thickness of tissue clamped by said end effector.

8. The surgical instrument of claim 6 wherein said cartridge body is pivotally supported within the end effector.

9. The surgical instrument of claim 8 wherein said opposing jaw members of said end effector comprise:
   an elongate channel configured to removably support the cartridge body therein; and
   an anvil movably supported relative to the elongate channel.

10. The surgical instrument of claim 9 wherein said elongate channel is configured to operably support a surgical fastener cartridge therein when said cartridge body of the measurement cartridge has been removed from the elongate channel.

11. The surgical instrument of claim 10 further comprising:
   a closure drive supported by said handle assembly and configured to generate said opening and closing motions for selective application to said end effector; and
   a firing drive supported by said handle assembly and configured to selectively generate and apply firing motions to said surgical fastener cartridge operably supported by said elongate channel.

12. The surgical instrument of claim 6 wherein said cartridge body includes a tissue clamping surface and wherein said nodule protrudes from said tissue clamping surface.

13. The surgical instrument of claim 6 wherein said first signal generator is located distal to said second signal generator.

14. The surgical instrument of claim 5 wherein said tissue thickness data is wirelessly transmitted to said display.

15. The surgical instrument of claim 5 wherein said display is supported on said handle assembly.

16. The surgical instrument of claim 5 wherein said display is remote from said handle assembly.

17. The surgical instrument of claim 5 further comprising a closure drive supported by said handle assembly and configured to generate said opening and closing motions for selective application to said end effector.

* * * * *